US007960334B2

(12) United States Patent
Gozes et al.

(10) Patent No.: US 7,960,334 B2
(45) Date of Patent: Jun. 14, 2011

(54) USE OF ADNF III POLYPEPTIDES FOR TREATING MENTAL DISEASES AND DISORDERS, INCLUDING SCHIZOPHRENIA

(75) Inventors: Illana Gozes, Ramat Hasharon (IL); Roy N. Alcalay, Tel Aviv (IL); Inna Divinski, Petach Tikva (IL); Eliezer Giladi, Netanya (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 89 days.

(21) Appl. No.: 10/547,986

(22) PCT Filed: Mar. 11, 2004

(86) PCT No.: PCT/IL2004/000232
§ 371 (c)(1),
(2), (4) Date: Apr. 10, 2006

(87) PCT Pub. No.: WO2004/080957
PCT Pub. Date: Sep. 23, 2004

(65) Prior Publication Data
US 2007/0054847 A1    Mar. 8, 2007

Related U.S. Application Data

(60) Provisional application No. 60/454,505, filed on Mar. 12, 2003.

(51) Int. Cl.
*A61K 38/00*    (2006.01)
*A61K 51/00*    (2006.01)
(52) U.S. Cl. ............................ 514/1.1; 530/300; 424/1.69
(58) Field of Classification Search ........................ 514/2
See application file for complete search history.

(56) References Cited

U.S. PATENT DOCUMENTS

| | | | |
|---|---|---|---|
| 4,587,046 A | 5/1986 | Goodman et al. | |
| 5,767,240 A | 6/1998 | Brenneman et al. | |
| 6,174,862 B1 | 1/2001 | Brenneman | |
| 6,613,740 B1 * | 9/2003 | Gozes et al. | 514/12 |
| 6,649,411 B2 | 11/2003 | Gozes et al. | |
| 6,933,277 B2 | 8/2005 | Brenneman et al. | |
| 7,264,947 B2 | 9/2007 | Gozes et al. | |
| 7,427,598 B2 | 9/2008 | Spong et al. | |
| 7,452,867 B2 | 11/2008 | Gozes et al. | |
| 7,863,247 B1 | 1/2011 | Brenneman et al. | |
| 2003/0166544 A1 | 9/2003 | Clark et al. | |
| 2004/0053313 A1 | 3/2004 | Gozes et al. | |
| 2008/0194488 A1 | 8/2008 | Gozes et al. | |
| 2009/0124543 A1 | 5/2009 | Gozes et al. | |
| 2009/0137469 A1 | 5/2009 | Gozes et al. | |
| 2009/0170780 A1 | 7/2009 | Gozes et al. | |
| 2009/0203615 A1 | 8/2009 | Spong et al. | |
| 2010/0216723 A1 * | 8/2010 | Gozes et al. | 514/15 |

FOREIGN PATENT DOCUMENTS

| | | |
|---|---|---|
| EP | 1 206 489 B1 | 5/2004 |
| WO | WO 92/18140 A1 | 10/1992 |
| WO | WO 96/11948 A1 | 4/1996 |
| WO | WO 98 35042 * | 8/1998 |
| WO | WO 98/35042 A1 | 8/1998 |
| WO | WO 00/27875 A2 | 5/2000 |
| WO | WO 00/53217 A2 | 9/2000 |
| WO | WO 01/12654 A2 | 2/2001 |
| WO | WO 01/92333 A2 | 12/2001 |
| WO | WO 2004/080957 A2 | 9/2004 |

OTHER PUBLICATIONS

Bassan, M. et al. "VIP-Induced Mechanism of Neuroprotection: The Complete Sequence of a Femtomolar-Acting Activity-Dependent Neuroprotective Protein." *Regulatory Peptides*, vol. 71, No. 2, (Aug. 15, 1997).
Bedikian, Agop Y., et al., "Phase II Trial of Docetaxel in Patients with Advanced Cutaneous Malignant Melanoma Previously Untreated with Chemotherapy:" Dec. 1995; *Journal of Clinical Oncology*; Vo. 13; No. 12; pp. 2895-2899.
Bassan, M. et al. "Complete Sequence of a Novel Protein Containing a Femtomolar-Activity-Dependent Neuroprotective Peptide." *Journal of Neurochemistry*, vol. 72, pp. 1283-1293 (1999).
Beni-Adani, L. et al. "Activity-Dependent Neurotrophic Protein is Neuroprotective in a Mouse Model of Closed Head Injury." Society for Neuroscience, 28th Annual Meeting, Los Angeles, CA, Nov. 7-12, 1998. Abstracts, vol. 23, Part 1, p. 1043 (1998).
Brenneman, D.C. and Gozes, I. "A Femtomolar-Acting Neuroprotective Peptide." *Journal of Clinical Investigation*, vol. 97, pp. 2299-2307 (1996).
Brenneman et al. "Neuronal Cell Killing by the Envelope Protein of HIV and Its Prevention by Vasoactive Intestinal Peptide." *Nature* 335:636 (1988). Brenneman et al. "N-Methyl-D-Aspartate Receptors Influence Neuronal Survival in Developing Spinal Cord Cultures" *Dev. Brain Res.* 51:63 (1990).
Brenneman, D.E. et al. "Identification of a Nine Amino Acid Core Peptide from Activity Dependent Neurotrophic Factor I." Society for Neuroscience, 27th Annual Meeting, New Orleans, LA, Oct. 25-30, 1997. Abstracts, vol. 23, Part 2, p. 2250 (1997).
Brenneman, D.E. et al. "Activity-Dependent Neurotrophic Factor: Structure-Activity Relationships of Femtomolar-Acting Peptides." *Journal of Pharmacology and Experimental Therapeutics*, vol. 285, pp. 619-627 (1998).
Brenneman, D.E., et al.; "Protective Peptides Derived from Novel Glial Proteins;" 2000; *Biochemical Society Transactions*; vol. 28; Part 4; pp. 452-455.

(Continued)

*Primary Examiner* — Maury Audet
(74) *Attorney, Agent, or Firm* — Kilpatrick Townsend & Stockton LLP

(57) ABSTRACT

This invention relates to the use of ADNF III polypeptides in the treatment of mental diseases or disorders, including schizophrenia. Embodiments of the invention provide methods for treating mental disorders, including schizophrenia, in a subject by administering a NAP, an 8-amino-acid peptide derived from Activity Dependent Neurotrophic Factor (ADNF III), in an amount sufficient to reduce or eliminate symptoms. The ADNF III polypeptides include polypeptides, analogs, subsequences, and D-amino acid versions (either wholly D-amino acid peptides or mixed D- and L-amino acid peptides), and combinations thereof which contain the active core sites and provide neuroprotective and anti-schizophrenic functions.

12 Claims, 3 Drawing Sheets

OTHER PUBLICATIONS

Chiba, Tomohiro et al.; "Neuroprotective Effect of Activity-Dependent Neurotrophic Factor Against Toxicity From Familial Amyotrophic Lateral Sclerosis-Linked Mutant SOD1 in Vitro and in Vivo"; 2004; *Journal of Neuroscience Research*, vol. 78, pp. 542-552.

Chiba, Tomohiro, et al., "Development of a Femtomolar-Acting Humanin Derivative Named Colivelin by Attaching Activity-Dependent Neurotropic Factor to its N Terminus: Characterization of Colivelin-Mediated Neuroprotection against Alzheimer's Disease-Relevant Insults in Vitro and in Vivo;" Nov. 2, 2005; *The Journal of Neuroscience*; vol. 25; No. 44; pp. 10252-10261.

Davidson, A. et al. "Protection Against Developmental Retardation and Learning Impairments in Apolipoprotein E-Deficient Mice by Activity-Dependent Femtomolar-Acting Peptides." Society for Neuroscience, 27th Annual Meeting, New Orleans, LA, Oct. 25-30, 1997. Abstracts, vol. 23, Part 2, p. 2250 (1997).

Dibbern, D.A., Jr. et al. "Inhibition of Murine Embryonic Growth by Human Immunodeficiency Virus Envelope Protein and Its Prevention by Vasoactive Intestinal Peptide and Activity-Dependent Neurotrophic Factor." *Journal of Clinical Investigation*, vol. 99, pp. 28377-2841 (1997).

Divinski, Inna, et al ., "A Femtomolar Acting Octapeptide Interacts with Tubulin and Protecots Astrocytes Against Zinc Intoxication;" *The Journal of Biological Chemistry*; Jul. 2, 2004; vol. 279, No. 27; pp. 28531-28538.

Furman, Sharon, et al.; "Subcellular Localization and Secretion of Activity-Dependent Neuroprotective Protein in Astrocytes;" 2004; *Neuron Glia Biology*; vol. 1; pp. 193-199.

GenBank Accession No. AB018327 from the DNA Data Bank of Japan (DDBJ) (released Nov. 17, 1998).

Giladi, E. "Protection Against Developmental and Learning Impairments in Apolipoprotein E-Deficient Mice by Activity-Dependent Femtomolar-Acting Peptides." *Neuroscience Letters*, Supplement 48 S1-S60, p. S19 (1997).

Glazner, G.W. et al. "A 9 Amino Acid Peptide Fragment of Activity-Dependent Neurotrophic Factor (ADNF) Protects Neurons from Oxidative Stress-Induced Death." Society for Neuroscience, 27th Annual Meeting, New Orleans, LA, Oct. 25-30, 1997. Abstracts, vol. 23, Part 2, p. 2249 (1997).

Glazner, G.W. et al. "Activity Dependent Neurotrophic Factor: A Potent Regulator of Embryonic Growth." *Anat. Embryol.* 200:65-71 (1999).

Gozes, I. and Brenneman, D.E. "Activity-Dependent Neurotrophic Factor (ADNF)." *Journal of Molecular Neuroscience*, vol. 7, pp. 235-244 (1996).

Gozes, I. at al. "Stearyl-Norleucine-Vasoactive intestinal Peptide (VIP): A novel VIP Analog for Noninvasive Impotence Treatment." *Endocrinology*, vol. 134, pp. 2125 (1994).

Gozes, I. et al. "Superactive Lipophilic Peptides Discriminate Multiple Vasoactive intestinal Peptide Receptors." *Journal of Pharmacology and Experimental Therapeutics*, vol. 273, pp. 161-167 (1995).

Gozes, I. et al. "Neuroprotective Strategy for Alzheimer Disease: Intranasal Administration of a Fatty Neuropeptide." *Proc. Natl. Acad. Sci. USA*, vol. 93, pp. 427-432 (1996).

Gozes I. et al. "Antiserum to Activity-Dependent Neurotrophic Factor Produces Neuronal Cell Death in CNS Cultures: Immunological and Biological Specificity." *Developmental Brain Research*, vol. 99, pp. 167-175 (1997).

Gozes, I. et al. A Femtomolar-Acting Activity-Dependent Neuroprotective Protein (ADNP). *Neuroscience Letters*, Supplement 48 S1-S60, p. S21 (1997).

Gozes, I. et al. "Protection Against Developmental Retardation in Apolipoprotein E-Deficient Mice by a Fatty neuropeptide: Implications for Early Treatment of Alzheimer's Disease." *Journal of Neurobiology*, vol. 33, pp. 329-342 (1997).

Gozes, I. et al. "The cDNA Structure of a Novel Femtomolar-Acting Neuroprotective Protein: Activity-Dependent-Neurotrophic Factor III (ADNFIII)." Society for Neuroscience, 27th Annual Meeting, New Orleans, LA, Oct. 25-30, 1997. Abstracts, vol. 23, Part 2, p. 2250 (1997).

Gozes, et al., "A Novel Signaling Molecule for Neuropeptide Action: Activity-dependent Neuroprotective Protein"; *Annals of the New York Academy of Sciences*, 897:125-135 (1999).

Gozes, I. et al. "Activity-dependent neurotrophic factor: Intranasal administration of femtomolar-acting peptides improve performance in a water maze" *Journal of Pharmacology and Experimental Therapeutics*, vol. 293, pp. 1091-1098 (2000).

Gozes, Illana, "Tubulin in the Nervous System;" 1982; *Neurochemistry International*; vol. 4; No. 23; pp. 101-120.

Gozes, Illana and Divinski, Inna; "The Femtomolar-Acting NAP Interacts with Microtubules: Novel Aspects of Astrocyte Protection;" 2004; *Journal of Alheimer's Disease*; vol. 6; pp. S37-S41.

Gozes, Illana; "Tau as a Drug Target in Alzheimer's Diseaase;" 2002; *Journal of Molecular Neuroscience*; vol. 19; pp. 337-338.

Gozes, Illana, et al.; "From Vasoactive Intestinal Peptide (VIP) Through Activity-Dependent Neuroprotective Protein (ADNP) to NAP;" 2003; *Journal of Moleculer Neuroscience*; vol. 20; pp. 315-322.

Gressens, P. et al. "Growth Factor Function of Vasoactive Intestinal Peptide in Whole Cultured Mouse Embryos." *Nature* 362:155-58 (1993).

Hannigan, J.H. and Berman, R.F. "Amelioration of Fetal Alcohol-Related Neurodevelopmental Disorders in Rats: Exploring Pharmacological and Environmental Treatments." *Neurotoxicol. & Teratol.* 22(1):103-111 (2000).

Hill, J.M. et al. "Learning Impairment in Adult Mice Produced by Early Embryonic Administration of Antiseum to Activity-Dependent Neurotrophic Factor (ADNF)." Society for Neuroscience, 27th Annual Meeting, New Orleans, LA, Oct. 25-30, 1997. Abstracts, vol. 23, Part 2, p. 2250 (1997).

Lagreze, Wolf A., et al.; "The Peptides ADNF-9 and NAP Increase Survival and Neurite Outgrowth of Rat Retinal Ganglion Cells in Vitro;" Mar. 2005; *Investigative Opthalmology & Visual Science*; vol. 46; No. 3; pp. 933-938.

Lee, Virginia M.-Y., et al., "Transgenic Animal Models of Taupathies;" 2005; *Biochimica et Biophysica Acta*; vol. 1739; pp. 251-259.

Lilling, G. et al. "Inhibition of Human Neuroblastoma Growth by a Specific VIP Antagonist." *Journal of Molecular Neuroscience*, vol. 5, pp. 231-239 (1995).

Mahato et al. "Development of Targeted Delivery Systems for Nucleic Acid Drugs." *J. of Drug Targeting* 4(6):337-357 (1997) [Abstract].

McKune, S.K. et al. "Localization of mRNA for Activity-Dependent Neurotrophic Factor III (ADNF III) in mouse Embryo and Adult CNS." Society for Neuroscience, 27th Annual Meeting, New Orleans, LA, Oct. 25-30, 1997. Abstracts, vol. 23, Part 2, p. 2249 (1997).

Nagase, et al., "Prediction of the Coding Sequences of Unidentified Human Genes. XI. The Complete Sequences of 100 New cDNA Clones from Brain Which Code for Large Proteins in vitro"; *DNA Research* 5:5:277-286 (1998).

Nelbock, P. et al. A cDNA for a Protein that Interacts with the Human Immunodeficiency Virus Tat Transactivator. *Science*, vol. 248, pp. 1650-1653 (1990).

Oberdoester, J. et al. "The Effects of Ethanol on Neuronal Cell Death: Implication for the Fetal Alcohol Syndrome." *FASEB Journal* 12(4):A134 (Mar. 17, 1998).

Pelsman, A. et al. "In Vitro Degeneration of Down Syndrome neurons is Prevented by Activity-Dependent Neurotrophic Factor-Derived Peptides." Society for Neuroscience, 28TH Annual Meeting, Los Angeles, CA, Nov. 7-12, 1998. Abstracts, vol. 24, p. 1044 (1998).

Skolnick, J. and Fetrow, J.S. "From Genes to Protein Structure and Function: Novel Applications of Computational Approaches in the Genomic Era." *Trends in Biotech.* 18(1):34-39 (2000).

Smith, A.E. "Viral Vectors in Gene Therapy." *Ann. Rev.Microbiol.* 49:807-838 (1995) [Abstract].

Smith-Swintosky, Virginia L., et al., "Activity-Dependent Neurotrophic Factor-9 and NAP Promote Neurite Outgrowth in Rat Hippocampal and Cortical Cultures;" 2005, *Journal of Molecular Neuroscience*; vol. 25; pp. 225-237.

Spinney, L. "New Peptides Prevent Brain Damage." *Molecular Medicine Today* 5(7):282 (Jul. 1999).

Spong et al. "Prevention of Fetal Alcohol Syndrome by Novel Peptides." *FASEB Journal* 13(5):A881 (Mar. 15, 1991).

Spong et al. "Prevention of Fetal Demise and Growth Restriction in a Mouse Model of Fetal Alcohol Syndrome" *The Journal of Pharmacology and Experimental Therapeutics* 297:774-779 (2001).

Van Gool, S.W., et al.; "Disease-and Treatment-Related Elevation of the Neurodegenerative Market Tau in Children with Hematological Malignancies;" 2000; *Leukemia*; vol. 14; pp. 2076-2084.

Voet et al. *Biochemistry, 2nd Ed.*, p. 67, (Mar. 1996).

Wilkemeyer et al. "Differential effects of ethanol antagonism and neuroprotection in peptide fragment NAPVSIPQ prevention of ethanol-induced developmental toxicity" *PNAS* 100:8543-8548 (2003).

Zemlyak, Ilona, et al.; "A Novel Peptide Prevents Death in Enriched Neuronal Cultures;" 2000; *Regulatory Peptides*; vol. 96; pp. 39-43.

* cited by examiner

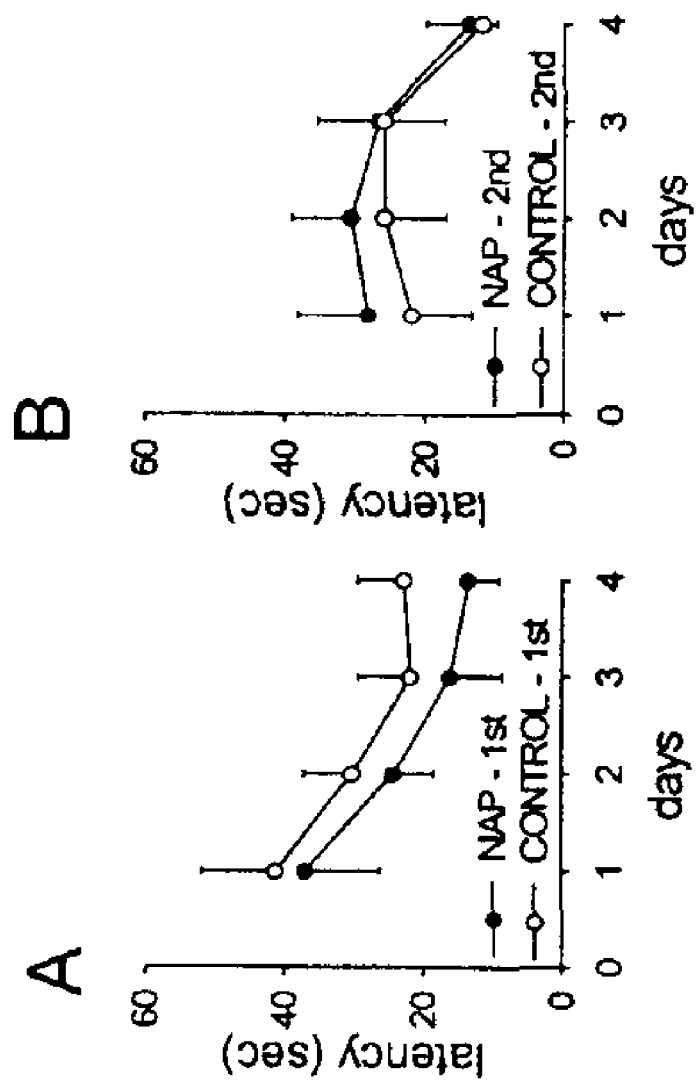

SEQUENCE LISTING

```
<160> NUMBER OF SEQ ID NOS: 23

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:activity
      dependent neurotrophic factor I (ADNF I) active
      core site (SAL, ADNF-9)

<400> SEQUENCE: 1

Ser Ala Leu Leu Arg Ser Ile Pro Ala
  1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence:activity
      dependent neurotrophic factor III (ADNF III,
      activity-dependent neuroprotective protein (ADNP))
      active core site (NAP)

<400> SEQUENCE: 2

Asn Ala Pro Val Ser Ile Pro Gln
  1               5

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 3

Val Leu Gly Gly Gly Ser Ala Leu Leu Arg Ser Ile Pro Ala
  1               5                  10

<210> SEQ ID NO 4
<211> LENGTH: 19
<212> TYPE: PRT
```

```
<213> ORGANISM: Artificial Sequence
<220> FEATURE:
<223> OTHER INFORMATION: Description of Artificial Sequence:ADNF
      polypeptide

<400> SEQUENCE: 4

Val Glu Glu Gly Ile Val Leu Gly Gly Gly Ser Ala Leu Leu Arg Ser
 1               5                  10                  15

Ile Pro Ala

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 5

Leu Gly Gly Gly Ser Ala Leu Leu Arg Ser Ile Pro Ala
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 6

Gly Gly Gly Ser Ala Leu Leu Arg Ser Ile Pro Ala
 1               5                  10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 7

Gly Gly Ser Ala Leu Leu Arg Ser Ile Pro Ala
 1               5                  10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 8

Gly Ser Ala Leu Leu Arg Ser Ile Pro Ala
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 9

Gly Gly Asn Ala Pro Val Ser Ile Pro Gln
```

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 10

Leu Gly Gly Asn Ala Pro Val Ser Ile Pro Gln Gln Ser
  1               5                  10

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 11

Leu Gly Leu Gly Gly Asn Ala Pro Val Ser Ile Pro Gln Gln Ser
  1               5                  10                  15

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 12

Ser Val Arg Leu Gly Leu Gly Gly Asn Ala Pro Val Ser Ile Pro Gln
  1               5                  10                  15

Gln Ser

<210> SEQ ID NO 13
<211> LENGTH: 88
<212> TYPE: PRT
<213> ORGANISM: Artificial Sequence
<220> FEATURE:
<223> OTHER INFORMATION: Description of Artificial Sequence:ADNF III
      polypeptide
<220> FEATURE:
<221> NAME/KEY: MOD_RES
<222> LOCATION: (1)..(40)
<223> OTHER INFORMATION: Xaa = any naturally occurring amino acid or
      known analogue of a natural amino acid, Xaa at positions
      1-40 may be present or absent
<220> FEATURE:
<221> NAME/KEY: MOD_RES
<222> LOCATION: (49)..(88)
<223> OTHER INFORMATION: Xaa = any naturally occurring amino acid or
      known analogue of a natural amino acid, Xaa at positions
      49-88 may be present or absent

<400> SEQUENCE: 13

Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa Xaa
                 20                  25                  30

Xaa Xaa Xaa Xaa Xaa Xaa Xaa Xaa Asn Ala Pro Val Ser Ile Pro Gln
             35                  40                  45

Xaa Xaa Xaa Xaa Xaa Xaa Xaa Xaa Xaa Xaa Xaa Xaa Xaa Xaa Xaa Xaa
 50                  55                  60

```
Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa
                85

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence:1-R or 2-R
      within the formula for ADNF I polypeptide

<400> SEQUENCE: 14

Val Leu Gly Gly Gly
 1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence:2-R within
      the formula for ADNF I polypeptide

<400> SEQUENCE: 15

Val Leu Gly Gly
 1

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence:2-R within
      the formula for ADNF I polypeptide

<400> SEQUENCE: 16

Val Leu Gly Gly Val
 1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence:2-R within
      the formula for ADNF I polypeptide

<400> SEQUENCE: 17

Gly Val Leu Gly Gly
 1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence:1-R within
      the formula for ADNF III polypeptide

<400> SEQUENCE: 18

Leu Gly Leu Gly Gly
 1               5

<210> SEQ ID NO 19
<211> LENGTH: 8
```

```
<212> TYPE: PRT
<213> ORGANISM: Artificial Sequence
<220> FEATURE:
<223> OTHER INFORMATION: Description of Artificial Sequence:1-R within
      the formula for ADNF III polypeptide

<400> SEQUENCE: 19

Ser Val Arg Leu Gly Leu Gly Gly
 1               5

<210> SEQ ID NO 20
<211> LENGTH: 89
<212> TYPE: PRT
<213> ORGANISM: Artificial Sequence
<220> FEATURE:
<223> OTHER INFORMATION: Description of Artificial Sequence:ADNF I
      polypeptide
<220> FEATURE:
<221> NAME/KEY: MOD_RES
<222> LOCATION: (1)..(40)
<223> OTHER INFORMATION: Xaa = any naturally occurring amino acid or
      known analogue of a natural amino acid, Xaa at positions
      1-40 may be present or absent
<220> FEATURE:
<221> NAME/KEY: MOD_RES
<222> LOCATION: (50)..(89)
<223> OTHER INFORMATION: Xaa = any naturally occurring amino acid or
      known analogue of a natural amino acid, Xaa at positions
      50-89 may be present or absent

<400> SEQUENCE: 20

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Ser Ala Leu Leu Arg Ser Ile Pro
         35                  40                  45

Ala Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa
                 85

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence:elongated
      NAP in Affi-Gel 10 NAP affinity chromatography

<400> SEQUENCE: 21

Lys Lys Lys Gly Gly Asn Ala Pro Val Ser Ile Pro Gln Cys
 1               5                  10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence:NAP in
      sulfolink coupling gel NAP affinity chromatography

<400> SEQUENCE: 22

Cys Lys Lys Gly Gly Asn Ala Pro Val Ser Ile Pro Gln
 1               5                  10
```

```
<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence:C2 control
      peptide

<400> SEQUENCE: 23

Val Leu Gly Gly Gly Ser Ala Leu Leu
 1               5
```

USE OF ADNF III POLYPEPTIDES FOR TREATING MENTAL DISEASES AND DISORDERS, INCLUDING SCHIZOPHRENIA

CROSS-REFERENCES TO RELATED APPLICATIONS

The present application claims priority to U.S. Ser. No. 60/454,505, filed Mar. 12, 2003, herein incorporated by reference in its entirety.

FIELD OF THE INVENTION

This invention relates to the use of ADNF polypeptides in the treatment of anxiety and/or depression. The present invention also relates to drug discovery assays using the ADNF polypeptide mechanism of action and target interaction, as well as the manufacture of medicaments, methods of application and formulation therefor. Embodiments of the invention provide methods for preventing and/or treating anxiety and depression disorders in a subject by administering a NAP, an 8-amino-acid peptide derived from Activity Dependent Neurotrophic Factor (ADNF III), in an amount sufficient to improve postnatal performance. The ADNF polypeptides include ADNF I and ADNF III (also referred to as ADNP) polypeptides, analogs, subsequences, and D-amino acid versions (either wholly D-amino acid peptides or mixed D- and L-amino acid peptides), and combinations thereof which contain their respective active core sites and provide neuroprotective and anti-anxiety functions.

BACKGROUND OF THE INVENTION

NAP, an 8-amino-acid peptide (NAPVSIPQ=Asn-Ala-Pro-Val-Ser-Ile-Pro-Gln; SEQ ID NO.2), is derived from a novel protein, activity-dependent neuroprotective protein, ADNP (U.S. Pat. No. 6,613,740, Bassan et al., *J. Neurochem.* 72: 1283-1293 (1999)). The NAP sequence within the ADNP gene is identical in rodents and humans (U.S. Pat. No. 6,613,740, Zamostiano, et al., *J. Biol. Chem.* 276:708-714 (2001)).

In cell cultures, NAP has been shown to have neuroprotective activity at femtomolar concentrations against a wide variety of toxins (Bassan et al., 1999; Offen et al., *Brain Res.* 854:257-262 (2000)). In animal models simulating parts of the Alzheimer's disease pathology, NAP was protective as well (Bassan et al., 1999; Gozes et al., *J. Pharmacol. Exp. Ther.* 293:1091-1098 (2000); see also U.S. Pat. No. 6,613,740). In normal aging rats, intranasal administration of NAP improved performance in the Morris water maze. (Gozes et al., *J. Mol. Neurosci.* 19:175-178 (2002). Furthermore, NAP reduced infarct volume and motor function deficits after ischemic injury, by decreasing apoptosis (Leker et al., *Stroke* 33:1085-1092 (2002)) and reducing damage caused by closed head injury in mice by decreasing inflammation (Beni Adani et al., *J. Pharmacol. Exp. Ther.* 296:57-63 (2001); Romano et, al., *J. Mol. Neurosci.* 18:37-45 (2002); Zaltzman et al., *NeuroReport* 14:481-484 (2003)). In a model of fetal alcohol syndrome, fetal death after intraperitoneal injection of alcohol was inhibited by NAP treatment (Spong et al., *J. Pharmacol. Exp. Ther.* 297:774-779 (2001); see also WO 00/53217). Utilizing radiolabeled peptides these studies showed that NAP can cross the blood-brain barrier and can be detected in rodents' brains either after intranasal treatment (Gozes et al., 2000) or intravenous injection (Leker et al, 2002) or intraperitoneal administration (Spong et al., 2001).

SUMMARY OF THE INVENTION

This invention discloses the surprising finding that NAP, and consequently, NAP related peptides, e.g., ADNF polypeptides, can provide novel therapeutic treatments for serious diseases and disorders, particularly anxiety disorders and mood disorders such as depression. This invention further discloses for the first time the molecular target for NAP, tubulin, a novel target platform for drug discovery, neuroprotection, anxiety and depression.

In one aspect, the present invention provides a method of treating or preventing anxiety or depression in a subject, the method comprising the step of administering a therapeutically effective amount of an ADNF polypeptide to a subject in need thereof.

In one embodiment, the ADNF polypeptide is a member selected from the group consisting of: (a) an ADNF I polypeptide comprising an active core site having the following amino acid sequence: Ser-Ala-Leu-Leu-Arg-Ser-Ile-Pro-Ala (SEQ ID NO:1); (b) an ADNF III polypeptide comprising an active core site having the following amino acid sequence (NAP): Asn-Ala-Pro-Val-Ser-Ile-Pro-Gln (SEQ ID NO:2); and (c) a mixture of the ADNF I polypeptide of part (a) and the ADNF III polypeptide of part (b).

In one embodiment, the ADNF polypeptide is a member selected from the group consisting of a full length ADNF I polypeptide, a full length ADNF III polypeptide (ADNP), and a mixture of a full length ADNF I polypeptide and a full length ADNF III polypeptide.

In one embodiment, the ADNF polypeptide is an ADNF I polypeptide. IN another embodiment, the active core site of the ADNF I polypeptide comprises at least one D-amino acid. In another embodiment, the active core site of the ADNF I polypeptide comprises all D-amino acids. In another embodiment, the ADNF I polypeptide is Ser-Ala-Leu-Leu-Arg-Ser-Ile-Pro-Ala (SEQ ID NO:1). In another embodiment, the ADNF I polypeptide comprises up to about 20 amino acids at at least one of the N-terminus and the C-terminus of the active core site. In another embodiment the ADNF I polypeptide is selected from the group consisting of:

```
                                              (SEQ ID NO:3)
Val-Leu-Gly-Gly-Gly-Ser-Ala-Leu-Leu-Arg-Ser-Ile-

Pro-Ala;

(SEQ ID NO:4)
Val-Glu-Glu-Gly-Ile-Val-Leu-Gly-Gly-Gly-Ser-Ala-

Leu-Leu-Arg-Ser-Ile-Pro-Ala;

(SEQ ID NO:5)
Leu-Gly-Gly-Gly-Ser-Ala-Leu-Leu-Arg-Ser-Ile-Pro-

Ala;

(SEQ ID NO:6)
Gly-Gly-Gly-Ser-Ala-Leu-Leu-Arg-Ser-Ile-Pro-Ala;

(SEQ ID NO:7)
Gly-Gly-Ser-Ala-Leu-Leu-Arg-Ser-Ile-Pro-Ala;

(SEQ ID NO:8)
Gly-Ser-Ala-Leu-Leu-Arg-Ser-Ile-Pro-Ala;
and (SEQ ID NO:1)
Ser-Ala-Leu-Leu-Arg-Ser-Ile-Pro-Ala.
```

In one embodiment, the ADNF polypeptide is an ADNP III polypeptide. In another embodiment, the ADNF polypeptide is a full length ADNF III polypeptide. In another embodiment, the ADNP III polypeptide is Asn-Ala-Pro-Val-Ser-Ile-Pro-Gln (SEQ ID NO:2). In another embodiment, the active core site of the ADNF III polypeptide comprises at least one D-amino acid. In another embodiment, the active core site of the ADNF III polypeptide comprises all D-amino acids. In another embodiment, the ADNF III polypeptide comprises up to about 20 amino acids at least one of the N-terminus and the C-terminus of the active core site. In another embodiment, the ADNF III polypeptide is a member selected from the group consisting of:

Gly-Gly-Asn-Ala-Pro-Val-Ser-Ile-Pro-Gln; (SEQ ID NO:9)

Leu-Gly-Gly-Asn-Ala-Pro-Val-Ser-Ile-Pro-Gln-Gln-Ser; (SEQ ID NO:10)

Leu-Gly-Leu-Gly-Gly-Asn-Ala-Pro-Val-Ser-Ile-Pro-Gln-Gln-Ser; (SEQ ID NO:11)

Ser-Val-Arg-Leu-Gly-Leu-Gly-Gly-Asn-Ala-Pro-Val-Ser-Ile-Pro-Gln-Gln-Ser; (SEQ ID NO:12)
and Asn-Ala-Pro-Val-Ser-Ile-Pro-Gln. (SEQ ID NO:2)

In one embodiment, at least one of the ADNF polypeptides is encoded by a nucleic acid that is administered to the subject.

In one embodiment, an ADNF I polypeptide and an ADNF III polypeptide are administered to the subject.

In one embodiment, the ADNF I or ADNF III polypeptide contains a covalently bound lipophilic moiety to enhance penetration or activity.

In one embodiment, the subject suffers from anxiety or depression. In another embodiment, the ADNF polypeptide is administered to prevent-anxiety or depression. In another embodiment, the disease is selected from the group consisting of: panic disorder, obsessive-compulsive disorder, post-traumatic stress disorder, social phobia, social anxiety disorder, specific phobias, generalized anxiety disorder, Major depression, dysthymia, and bipolar disorder.

In one embodiment, the ADNF polypeptide is administered intranasally. In another embodiment, the ADNF polypeptide is administered orally. In another embodiment, the ADNF polypeptide is administered intravenously or subcutaneously.

In one aspect, the present invention provides use of an ADNF polypeptide in the manufacture of a medicament for the treatment of depression or anxiety.

In one aspect, the present invention provides the use of the NAP-tubulin binding site(s) to identify anxiolytic drugs and drugs that alleviate depression and provide neuroprotection.

BRIEF DESCRIPTION OF THE DRAWINGS

FIG. 3. NAP effects in the Morris water maze. Mice were subjected to two daily tests in the Morris water maze, and latency to reach the hidden platform over a 90 sec test period was recorded, A and B—15-months-old mice chronically treated (week days, daily for 7 months) with intranasal NAP applications in comparison to control mice (A—first daily trial and B-second daily trial). Results show the latency to find the hidden platform. NAP treated mice, n=11; control mice, n=10.

DEFINITIONS

Figure 1:
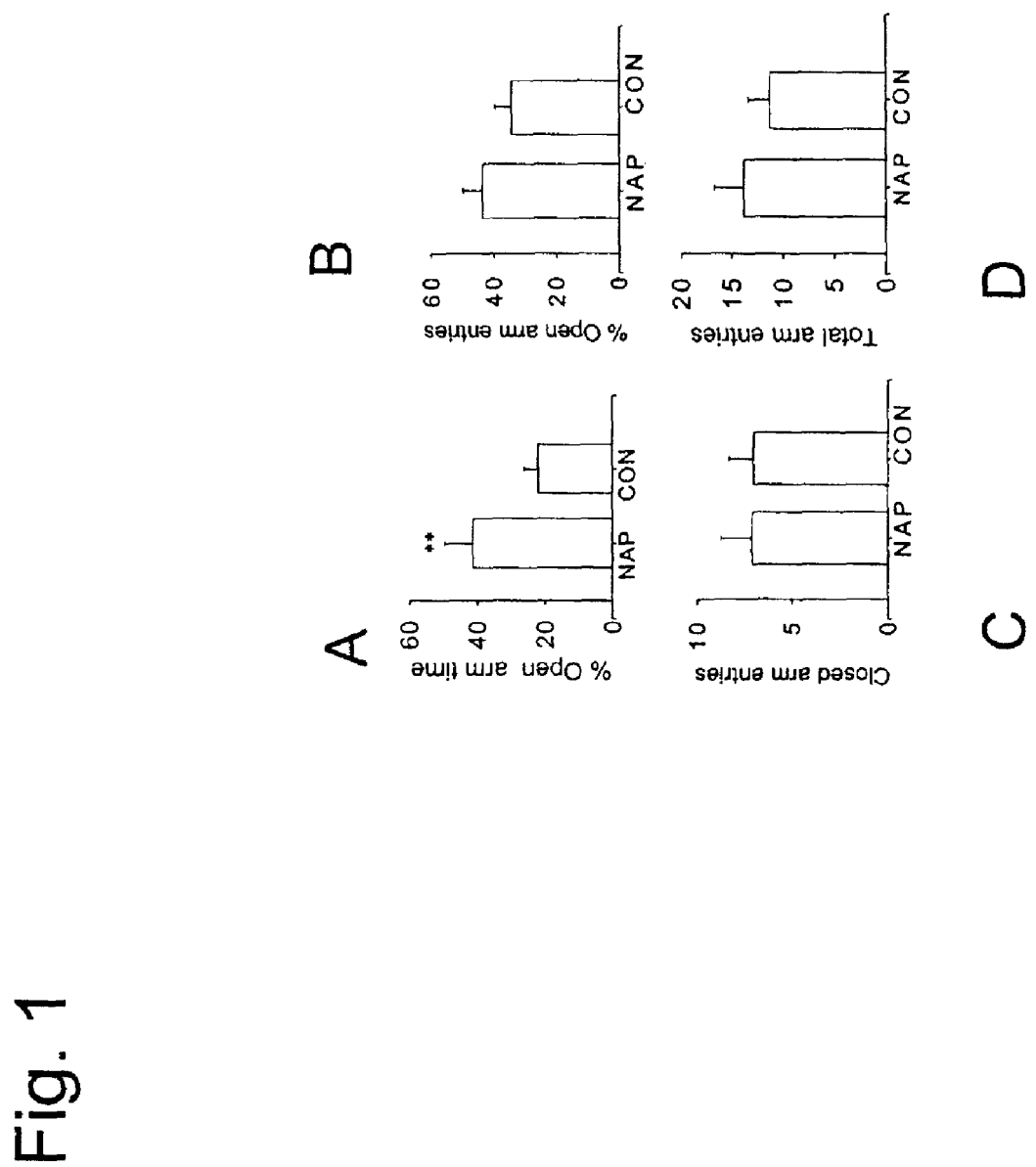
FIG. 1. NAP-treated mice are more relaxed than sham-treated mice. Elevated plus maze tests were performed on 13-month-old mice chronically treated (week days, daily for 5 months) with intranasal NAP (n=12) in comparison to controls (n=12). The maze (elevated above ground level) was in a "plus" form with 2 open arms and 2 closed arms. Each mouse was placed separately in the center of the maze, facing an open arm. Parameters measured (over a 5 min test period) included: A—percent tire spent in the open arms; B—percent open arms entries, C—number of closed arms entries; D—total number of arms entries. (**p<0.01).

The phrase "ADNF polypeptide" refers to one or more activity dependent neurotrophic factors (ADNF) that have an active core site comprising the amino acid sequence of SALLRSIPA (SEQ ID NO.1) (referred to as "SAL") or NAPVSIPQ (SEQ ID NO:2) (referred to as "NAP"), or conservatively modified variants thereof that have neurotrophic/neuroprotective activity as measured with in vitro cortical neuron culture assays described by, e.g., Hill et al., *Brain Res.* 603:222-233 (1993); Brenneman & Gozes, *J. Clin. Invest.* 97:2299-2307 (1996), Forsythe & Westbrook, *J. Physiol. Lond.* 396:515 (1988). An ADNF polypeptide can be an ADNF I polypeptide, an ADNF III polypeptide, their alleles, polymorphic variants, analogs, interspecies homolog, any subsequences thereof (e.g., SALLRSIPA (SEQ ID NO:1) or NAPVSIPQ (SEQ ID NO:2)) or lipophilic variants that exhibit neuroprotective/neurotrophic action on, e.g., neurons originating in the central nervous system either in vitro or in vivo. An "ADNF polypeptide" can also refer to a mixture of an ADNF I polypeptide and an ADNF III polypeptide.

The term "ADNF I" refers to an activity dependent neurotrophic factor polypeptide having a molecular weight of about 14,000 Daltons with a pI of 8.3±0.25. As described above, ADNF I polypeptides have an active site comprising an amino acid sequence of Ser-Ala-Leu-Leu-Arg-Ser-Ile-Pro-Ala (also referred to as "SALLRSIPA" (SEQ ID NO:1) or "SAL" or "ADNF-9"). See Brenneman & Gozes, *J. Clin. Invest.* 97:2299-2307 (1996), Glazner et al., *Anat. Embryol.* ((Berl). 200:65-71 (1999), Brenneman et al., *J. Pharm. Exp. Ther.*, 285:619-27 (1998), Gozes & Brenneman, *J. Mol. Neurosci.* 7:235-244 (1996), and Gozes et al., *Dev. Brain Res.* 99:167-175 (1997), all of which are herein incorporated by reference. Unless indicated as otherwise, "SAL" refers to a peptide having an amino acid sequence of Ser-Ala-Leu-Leu-Arg-Ser-Ile-Pro-Ala (SEQ ID NO:1), not a peptide having an amino acid sequence of Ser-Ala-Leu. A full length amino acid sequence of ADNF I can be found in WO 96/11948, herein incorporated by reference in its entirety.

The phrase "ADNF III polypeptide" or "ADNF III" also called activity-dependent neuroprotective protein (ADNP) refers to one or more activity dependent neurotrophic factors (ADNF) that have an active core site comprising the amino acid sequence of NAPVSIPQ (SEQ ID NO:2) (referred to as "NAP"), or conservatively modified variants thereof that have neurotrophic/neuroprotective activity as measured with in vitro cortical neuron culture assays described by, e.g., Hill et al., *Brain Res.* 603, 222-233 (1993); Gozes et al., *Proc. Natl. Acad. Sci. USA* 93, 427-432 (1996). An ADNF polypeptide can be an ADNF III polypeptide, allelelic or polymorphic variant, analog, interspecies homolog, or any subsequences thereof (e.g., NAPVSIPQ; SEQ ID NO:2) that exhibit neuroprotective/neurotrophic action on, e.g., neurons originating in the central nervous system either in vitro or in vivo. ADNF III polypeptides can range from about eight amino acids and can have, e.g., between 8-20, 8-50, 10-100 or about 1000 or more amino acids.

Full length human ADNF III has a predicted molecular weight of 123,562.8 Da (>1000 amino acid residues) and a pI of about 6.97. As described above, ADNF III polypeptides have an active site comprising an amino acid sequence of Asn-Ala-Pro-Val-Ser-Ile-Pro-Gln (also referred to as "NAPVSIPQ" (SEQ ID NO:2) or "NAP"). See Zamostiano et al., *J. Biol. Chem.* 276:708-714 (2001) and Bassan et al., *J. Neurochem.* 72:1283-1293 (1999), each of which is incorporated herein by reference. Unless indicated as otherwise, "NAP" refers to a peptide having an amino acid sequence of Asn-Ala-Pro-Val-Ser-Ile-Pro-Gln (SEQ ID NO:2), not a peptide having an amino acid sequence of Asn-Ala-Pro. Full-length amino acid and nucleic acid sequences of ADNF III can be found in WO 98/35042, WO 00/27875, U.S. Pat. Nos. 6,613,740 and 6,649,411. The Accession number for the human sequence is NP_852107, see also Zamostiano et al., supra.

The term "subject" refers to any mammal, in particular human, at any stage of life. The term "contacting" is used herein interchangeably with the following: combined with, added to, mixed with, passed over, incubated with, flowed over, etc. Moreover, the ADNF III polypeptides or nucleic acids encoding them of the present invention can be "administered" by any conventional method such as, for example, parenteral, oral, topical, and inhalation routes. In some embodiments, parenteral and nasal inhalation routes are employed.

A "mental disorder" or "mental illness" or "mental disease" or "psychiatric or neuropsychiatric disease or illness or disorder" refers to mood disorders (e.g., major depression, mania, and bipolar disorders), psychotic disorders (e.g., schizophrenia, schizoaffective disorder, schizophreniform disorder, delusional disorder, brief psychotic disorder, and shared psychotic disorder), personality disorders, anxiety disorders (e.g., obsessive-compulsive disorder and attention deficit disorders) as well as other mental disorders such as substance-related disorders, childhood disorders, dementia, autistic disorder, adjustment disorder, delirium, multi-infarct dementia, and Tourette's disorder as described in Diagnostic and Statistical Manual of Mental Disorders, Fourth Edition, (DSM IV). Typically, such disorders have a complex genetic and/or a biochemical component.

A "mood disorder" refers to disruption of feeling tone or emotional state experienced by an individual for an extensive period of time. Mood disorders include major depression disorder (i.e., unipolar disorder), ma, dysphoria, bipolar disorder, dysthymia, cyclothymia and many others. See, e.g., *Diagnostic and Statistical Manual of Mental Disorders*, Fourth Edition, (DSM IV).

"Major depression disorder," "major depressive disorder," or "unipolar disorder" refers to a mood disorder involving any of the following symptoms: persistent sad, anxious, or "empty" mood; feelings of hopelessness or pessimism; feelings of guilt, worthlessness, or helplessness; loss of interest or pleasure in hobbies and activities that were once enjoyed, including sex; decreased energy, fatigue, being "slowed down"; difficulty concentrating, remembering, or making decisions; insomnia, early-morning awakening, or oversleeping; appetite and/or weight loss or overeating and weight gain; thoughts of death or suicide or suicide attempts; restlessness or irritability, or persistent physical symptoms that do not respond to treatment, such as headaches digestive disorders, and chronic pain. Various subtypes of depression are described in, e.g., DSM IV.

"Bipolar disorder" is a mood disorder characterized by alternating periods of extreme moods. A person with bipolar disorder experiences cycling of moods that usually swing try being overly elated or irritable (mania) to sad and hopeless (depression) and then back again, with periods of normal mood in between. Diagnosis of bipolar disorder is described in, e.g., DSM IV. Bipolar disorders include bipolar disorder I (mania with or without major depression) and bipolar disorder II (hypomania with major depression), see, e.g., DSM IV.

"Anxiety," "anxiety disorder," and "anxiety-related' disorder refer to psychiatric syndromes characterized by a subjective sense of unease, dread, or foreboding, e.g., panic disorder, generalized anxiety disorder, attention deficit disorder, attention deficit hyperactive disorder, obsessive-compulsive disorder, and stress disorders, e.g., acute and post-traumatic. Diagnostic criteria for these disorders are well known to those of skill in the art (see, e.g., *Harrison's Principles of Internal Medicine*, pp. 2486-2490 (Wilson et al., eds., 12th ed. 1991) and DSM IV).

The terms "polypeptide," "peptide" and "protein" are used interchangeably herein to refer to a polymer of amino acid residues. Generally, a peptide refers to a short polypeptide. The terms apply to amino acid polymers in which one or more amino acid residue is an analog or mimetic of a corresponding naturally occurring amino acid, as well as to naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. For the purposes of this application, amino acid analogs refers to compounds that have the same basic chemical structure as a naturally occurring amino acid, i.e., an a carbon that is bound to a hydrogen a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in WO 01/12654, incorporated herein by reference, which may improve oral availability and other drug like characteristics of the compound. In such embodiments, one or more, and potentially all of the amino acids of NAP or the ADNF-polypeptide will have D-chirality. The therapeutic use of peptides can be enhanced by using D-amino acids to provide longer half life and duration of action. However, many receptors exhibit a strong preference for L-amino acids, but examples of D-peptides have been reported that have equivalent activity to the naturally occurring L-peptides, for example, pore-forming antibiotic peptides, beta amyloid peptide (no change in toxicity), and endogenous ligands for the CXCR4 receptor. In his regard, NAP and ADNF polypeptides also retain activity in the D-amino acid form (Brenneman et al. *J. Pharmacol. Exp. Ther.* (2004), in press, see also Brenneman et al., *The of*

*Pharmacology and Experimental Therapeutics Fasy Forward*, Mar. 8, 2004; 10.1124/jpet103.063891).

Amino acids may be referred to by either their commonly known three letter symbols or by the one-letter symbols recommended by the IUPAC-IUB Biochemical Nomenclature Commission. Nucleotides, likewise, may be referred to by their commonly accepted single-letter codes. The amino acids referred to herein are described by shorthand designations as follows:

TABLE I

Amino Acid Nomenclature

| Name | 3-letter | 1 letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991; Ohtsuka et al. *J. Biol. Chem.* 260:2605-2608 (1985); Rossolini et al., *Mol. Cell Probes* 8:19-98 (1994)). Because of the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar-amino acid. Conservative substitution-tables providing functionally similar amino acids are well known in the art. Such conservatively modified variants are in addition to and do not exclude polymorphic variants, interspecies homologs, and alleles of the invention.

The following groups each contain amino acids that are conservative substitutions for one another:
1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (I);
7) Isoleucine (1), Leucine (L), Valine (V); and
8) Phenylalanine (F), Tyrosine (Y), Tryptophan (W). (see, e.g., Creighton, *Proteins* (1984)).

One of the skills in the art will appreciate that many conservative variations of the nucleic acid and polypeptide sequences provided herein yield functionally identical products. For example, due to the degeneracy of the genetic code, "silent substitutions" (i.e., substitutions of a nucleic acid sequence that do not result in an alteration in an encoded polypeptide are an implied feature of every nucleic acid sequence that encodes an amino acid. Similarly, "conservative amino acid substitutions," in one or a few amino acids in an amino acid-sequence are substituted with different amino acids with highly similar properties (see the definitions section, supra), are also readily identified as being highly similar to a disclosed no acid sequence, or to a disclosed nucleic acid sequence that encodes an amino acid. Such conservatively substituted variations of each explicitly listed nucleic acid and amino acid sequences are a feature of the present invention.

The terms "isolated," "purified" or "biologically pure" refer to material that is substantially or essentially free from components that normally accompany it as found in its native state.

"An amount sufficient" or "an efficient amount" or a "therapeutically effective amount" is that amount given NAP or ADNF polypeptide that exhibits the anxiolytic or anti-depressant activity of interest or which provides either a subjective relief of a symptom(s) or an objectively identifiable improvement as noted by the clinician or other qualified observer. In therapeutic applications, the NAP or ADNF polypeptides of the invention are administered to a patient in an amount sufficient to reduce or eliminate symptoms of anxiety and/or depression. An amount adequate to accomplish this is defined as the "therapeutically effective dose." The dosing range varies with the NAP or ADNF polypeptide, as further set out below, and in CA patent 2202496, U.S. Pat. No. 6,174,862 and U.S. Pat. No. 6,613,740, herein incorporated by reference in their entirety.

"Inhibitors," "activators," and "modulators" of expression or of activity are used to refer to inhibitory, activating, or modulating molecules, respectively, identified using in vitro and in vivo assays for expression or activity, e.g., ligands, agonist and their homologs and mimetics. The term "modulator" includes inhibitors and activators. Inhibitors are agents that, e.g., inhibit expression of a polypeptide or polynucleotide of the invention or bind to, partially or totally block stimulation or enzymatic activity, decrease, prevent, delay activation, inactive, desensitize, or down regulate the activity of a polypeptide or polynucleotide of the invention, e.g., antagonists. Activators are agents that, e.g., induce or activate the expression of a polypeptide or polynucleotide of the invention or bind to, stimulate, increase, open, activate, facilitate, enhance activation or enzymatic activity, sensitize or up regulate the activity of polypeptide or polynucleotide of the invention, e.g., agonists. Modulators include naturally occurring and synthetic ligands, antagonists, agonists, small chemical molecules and the like. Assays to identify inhibitors and activators include, e.g., applying putative modulator compounds to cells, in the presence or absence of a polypeptide or polynucleotide of the invention and then determining the functional effects on a polypeptide or polynucleotide of the invention activity. Samples or assays comprising a polypeptide or polynucleotide of the invention that are treated with a potential activator, inhibitor, or modulator are compared to control samples without the inhibitor, activator, or modulator to examine the extent of the effect. Control samples (untreated with modulators) are assigned a relative activity value of 100%. Inhibition is achieved when the activity value of a polypeptide or polynucleotide of the invention relative to the control is about 80%, optionally 50% or 25-1%. Activation is achieved when the activity value of a polypeptide or polynucleotide of the invention relative toe the control is 110%, optionally 150%, optionally 200-500%, or 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, such as a combinatorial or randomized library that provides a sufficient range of diversity. Test compounds are optionally linked to a fusion partner, e.g., targeting compounds, rescue compounds dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 Daltons and less than about 2500 Daltons, preferably less than about 2000 Daltons, preferably between about 100 to 1000 Daltons, more preferably between about 200 to about 500 Daltons.

DETAILED DESCRIPTION OF THE INVENTION

This invention relates to the therapeutic use of NAP and ADNF polypeptides in the treatment of diseases and disorders including anxiety and depression, and disorders related thereto. The invention is based on the finding set out in Example 1 that treatment of mice with NAP peptide significantly reduces anxiety-like behavior in a widely used and accepted industry standard model of anxiety, the Elevated plus-maze (see Rodgers & Dalvi, *Neurosci. Biobehav. Rev.* 21(6) 801-801(1997)). The invention further discloses that while providing anxiolytic effects, NAP does not inhibit cognitive functions. In another embodiment, this invention further discloses NAP's mechanism of action provides drug assays for compounds that also can be used to treat anxiety and depression. In such assays, compounds that modulate the interaction between NAP and tubulin are identified.

ADNF Polypeptides

In one embodiment the ADNF polypeptides of the present invention comprise the following amino acid sequence: $(R^1)_x$-Asn-Ala-Pro-Ser-Ile-Pro-Gln-$(R^2)_y$(SEQ ID NO: 13) and conservatively modified variations thereof. In this designations, $R^1$ denotes the orientation of the amino terminal ($NH_2$ or N-terminal) end and $R^2$ represents the orientation of the carboxyl terminal (COOH or C-terminal) end.

In the above formula, $R^1$ is an amino acid sequence comprising from 1 to about 40 amino acids, wherein each amino acid is independently selected from the group consisting of naturally occurring amino acids and amino acid analogs. The term "independently selected" is used herein to indicate that the amino acids making up the amino acid sequence $R^1$ may be identical or different (e.g., all of the amino acids making up the amino sequence may be threonine, etc.). Moreover, as previously explained, the amino acids making up the amino acid sequence $R^1$ may be either naturally occurring amino acids, or known analogues of natural amino acids that functions in a manner similar to the naturally occurring amino acids (i.e., amino acid mimetics and analogs). Suitable amino acids that can be used to form the amino acids sequence $R^1$ include, but are not limited to, those listed in Table I, infra. The indexes "x" and "y" are independently selected and can be equal to one or zero.

As with $R^1$, $R^2$, in the above formula, is an amino acid sequence comprising from 1 to 40 amino acids, wherein each amino acid is independently selected from the group consisting of naturally occurring amino acids and amino acid analogs. Moreover, as with $R^1$, the amino acids making up the amino acid sequence $R^2$ may be identical or different, and may be either naturally occurring amino acids, or known analogues of natural amino acids that function in a manner similar to the naturally occurring amino acids (i.e., amino acid mimetics and analogs). Suitable amino acids that can be used to form $R^2$ include, but are not limited to, those listed in Table I, infra.

As used herein, "NAP" or "NAP peptide" refers to the formula above where x and y both equal 0. "NAP related peptide" refers to any of the other variants of NAP which are described the formula.

$R^1$ and $R^2$ are independently selected. If $R^1 R^2$ are the same, they are identical in terms of both chain length and amino acid composition. For example, both $R^1$ and $R^2$ may be Val-Leu-Gly-Gly-Gly (SEQ ID NO:14). If $R^1$ and $R^2$ are different, they can differ from one another in terms of chain length and/or amino acid composition and/or order of amino acids in the amino acids sequences. For example, $R^1$ may be Val-Leu-Gly-Gly-Gly (SEQ ID NO:14), whereas $R^2$ may be Val-Leu-Gly-Gly (SEQ ID NO:15). Alternatively, $R^1$ may be Val-Leu-Gly-Gly-Gly (SEQ ID NO:14), whereas $R^2$ may be Val-Leu-Gly-Gly-Val (SEQ ID NO:16). Alternatively, $R^1$ may be Val-Leu-Gly-Gly-Gly (SEQ ID NO:14), whereas $R^2$ may be Gly-Val-Leu-Gly-Gly (SEQ ID NO:17).

Within the scope of the above formula, certain NAP and NAP related polypeptides are preferred, namely those in which x and y are both zero (i.e. NAP). Equally preferred are NAP and NAP related polypeptides in which x is one; $R^1$ Gly-Gly; and y is zero (SEQ ID NO:9). Also equally preferred are NAP and NAP related polypeptides in which x is one; $R^1$ is Leu-Gly-Gly; y is one; and $R^2$ is -Gln-Ser (SEQ ID NO:10). Also equally preferred are NAP and NAP related polypeptides in which x is one; $R^1$ is Leu-Gly-Leu-Gly-Gly- (SEQ ID NO:18); y is one; and $R^2$ is -Gln-Ser (SEQ ID NO:11). Also equally preferred are NAP and NAP related polypeptides in which x is one; $R^1$ is Ser-Val-Arg-Leu-Gly-Leu-Gly-Gly- (SEQ ID NO:19); y is one; and $R^2$ is -Gln-Ser (SEQ ID NO:12). Additional amino acids can be added to both the N-terminus and the C-terminus of the active peptide without loss of biological activity.

In another aspect, the present invention provides pharmaceutical compositions comprising one of the previously described NAP and NAP related polypeptides in an amount sufficient to exhibit anxiolytic (e.g. anxiety reducing) or anti-depressant activity, in a pharmaceutically acceptable diluent, carrier or excipient. In one embodiment, the NAP or NAP related peptide has an amino acid sequence selected from the group consisting of SEQ ID NO:2, and 9-12, and conservatively modified variations thereof.

In another embodiment, the ADNF polypeptide comprises the following amino acid sequence: $(R^1)_x$-Ser-Ala-Leu-Leu-Arg-Ser-Ile-Pro-Ala-$(R^2)_y$ (SEQ ID NO:20) and conservatively modified variations thereof. In this designation, $R^1$ denotes the orientation of the amino terminal ($NH_2$ or N-terminal) end and $R^2$ represents the orientation of the carboxyl terminal (COOH or C-terminal) end.

In the above formula, $R^1$ is an amino acid sequence comprising from 1 to about 40 amino acids, wherein each amino acid is independently selected from the group consisting of naturally occurring amino acids and amino acid analogs. The term "independently selected" is used herein to indicate that the amino acids making up the amino acid sequence $R^1$ may be identical or different (e.g., all of the amino acids in the amino acid sequence may be threonine, etc). Moreover, as previously explained, the amino acid making up the amino acid sequences $R^1$ may be either naturally occurring amino acids, or known analogues of natural amino acids that functions in a manner similar to naturally occurring amino acids (i.e., amino acid mimetics and analogs). Suitable amino acids that can be used to form the amino acid sequence $R^1$ include, but are not limited to, those listed in Table I, infra. The indexes "x" and "y" are independently selected and can be equal to one or zero.

As with $R^1$, $R^2$, in the above formula, is an amino acid sequence comprising from 1 to about 40 amino acids, wherein each amino acid is independently selected form the groups consisting of naturally occurring amino acids and amino acid analogs. Moreover, as with $R^1$, the amino acids making up the amino acid sequence $R^2$ may be identical or different, and may be either naturally occurring amino acids, or known analogues of natural amino acids that functions in a manner similar to the naturally occurring amino acids (i.e., amino acid mimetics and analogs). Suitable amino acids that can be used to form $R^2$ include, but are not limited to those listed in Table I, infra.

As used herein, "SAL" or "SAL peptide" refers to the formula above where x and y both equal 0. "SAL related peptide" refers to any of the other variants of SAL which are described the formula.

$R^1$ and $R^2$ are independently selected. If $R^1R^2$ are the same, they are identical in terms of both chain length and amino acid composition. Additionally amino acids can be added to both the N-terminus and the C-terminus of the active peptide without loss of biological activity.

In an another aspect, the present invention provides pharmaceutical compostions comprising on of the previously described SAL and SAL-related polypeptides in an amount sufficient to exhibit anxiolytic (e.g., anxiety reducing) or anti-depressant activity, in a pharmaceutically acceptable diluent, carrier or excipient. In one embodiment, the SAL or SAL related peptide has an amino acid sequence selected form the group consisting of SEQ ID NO:1 and 3-8, and conservatively modified variations thereof.

Design and Synthesis of ADNF Polypeptides

Polypeptides and peptides comprising the core NAPV-SIPQ (SEQ ID NO:2) or SALLRSIPA (SEQ ID NO:1) active site can be easily made, e.g., by systematically adding one amino acid at a time and screening the resulting peptide for biological activity, as described herein. In addition, the contributions made by the side chains of various amino acid residues in such peptides can be probed via a systematic scan with a specified amino acid, e.g., Ala.

One of skill will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques (see Giliman & Smith, Gene 8:81-97 (1979); Roberts et al., Nature 328:731-734 (1987)).

Most commonly, polypeptide sequences are altered by changing the corresponding nucleic acid sequence and expressing the polypeptide. However, polypeptide sequences are also optionally generated synthetically using commercially available peptide synthesizers to produce any desired polypeptide (see Merrifield, Am. Chem. Soc. 85:2149-2154 (1963); Stewart & Young, Solid Phase Peptide Synthesis (2nd ed. 1984)).

One of skill can select a desired nucleic acid or polypeptide of the invention based upon the sequences provided and upon knowledge in the art regarding proteins generally. Knowledge regarding the nature of proteins and nucleic acids allows one of skill to select appropriate sequences with activity similar or equivalent to the nucleic acids and polypeptides disclosed herein. The definitions section, supra, describes exemplar conservative amino acid substitutions.

Modifications to the NAP and ADNF polypeptides are evaluated by routine screening techniques in suitable assays for the desired characteristic. For instance, changes in the immunological character of a polypeptide can be detected by an appropriate immunological assay. Modifications of other properties such as nucleic acid hybridization to a target nucleic acid, redox or thermal stability of a protein, hydrophobicity, susceptibility to proteolysis, or the tendency to aggregate are all assayed according to standard techniques.

More particularly, it will be readily apparent to those of ordinary skill in the art that the small peptides of the present invention can readily be screened for anxiolytic and anti-depressant activity by employing suitable assays and animal models known to those skilled in the art. Among the animal models employed to evaluate the anxiolytic or anxiogenic effects of drugs, the elevated plus-maze is probably the most popular. (See Rodgers and Dalvi, supra). For factors controlling measures of anxiety and responses to novelty in the mouse, see File, Behav. Brain Res. 125:151-157 (2001). For a review of the validity and variability of the elevated plus-maze as an animal model of anxiety, see Hogg, Pharmacol. Biochem. Behav. 54:21-30 (1996); and Lister, Psychopharmacology (Berlin) 92: 180-185 (1987). The Elevated plus-maze model is described in some detail in Example 1. Still, those skilled in the art are aware of a wide range of alternative models which are also available to measure the anxiolytic effect of therapeutic agents. Such models nay require measurement of physiological or endocrine functions (e.g., hyperthermic or corticosterone responses to stress) while others analyze behavior. Broadly speaking, suitable behavioral models for testing anxiolytic effects of a test compound involve exposure of animals to stimuli (exteroceptive or interoceptive) that appear capable of causing anxiety in humans. The animals are then treated with the test compound to determine if it generates an anxiolytic effect. The models may also be grouped into two general categories involving either conditioned (e.g. Geller-Seifter conflict, potentiated startle) or unconditioned (social interaction and light/dark exploration tests) responses. Those in the art are aware that any of these standard behavioral models may be used to test NAP or ADNF polypeptides to identify or confirm anxiolytic activity of test peptides.

Using these assays and models, one of ordinary skill in the art can readily prepare a large number of NAP and ADNF polypeptides in accordance with the teachings of the present invention and, in turn, screen them using the foregoing animal models to find ADNF polypeptides, in addition to those set forth herein, which possess the desired activity. For instance, using the NAP peptide (i.e., Asn-Ala-Pro-Val-Ser-Ile-Pro-Gln (SEQ ID NO:2)) or SAL peptide Ser-Ala-Leu-Lou-Arg-Ser-Ile-Pro-Ala (SEQ ID NO:1) as a starting point, one can systematically add, for example, Gly-, Gly-Gly-, Leu-Gly-Gly- to the N-terminus of the peptide and, in turn, screen each of these NAP or ADNP polypeptides in the foregoing assay to determine whether they possess anxiolytic or anti-depressant activity. In doing so, it will be found that additional amino acids can be added to both the N-terminus and the C-terminus of the active site, i.e., Asn-Ala-Pro-Val-Ser-Ile-Pro-Gln (SEQ ID NO:2) or Ser-Ala-Leu-Leu-Arg-Ser-Ile-Pro-Ala (SEQ ID NO:1), without loss of biological activity.

The peptides of the invention may be prepared via a wide variety of well-known techniques. Peptides of relatively short size are typically synthesized on a solid support or in solution in accordance with conventional techniques (see, e.g., Merrifield, *Am. Chem. Soc.* 85:2149-2154 (1963). Various automatic synthesizers and sequencers are commercially available and can be used in accordance with known protocols (see, e.g., Stewart & Young, *Solid Phase Peptide Synthesis* (2nd 1984)). Solid phase synthesis in which the C-terminal amino acid of die sequence is attached to an insoluble support followed by sequential addition of the remaining amino acids in the sequence is the preferred method for the chemical synthesis of the peptides of this invention. Techniques for solid phase synthesis are described by Barany & Merrifield, *Solid-Phase Peptide Synthesis*; pp. 3-284 in *The Peptides: Analysis, Synthesis, Biology*, Vol. 2: *Special Methods in Peptide Synthesis*, Part A.; Merrifield et al 1963; Stewart et al. 1984). NAP and related peptides are synthesized using standard Fmoc protocols (Wellings & Atherton, *Methods Enzymol.* 289:44-67 (1997)).

In addition to the foregoing techniques, the peptides for use in the invention may be prepared by recombinant DNA methodology. Generally, this involves creating a nucleic acid sequence that encodes the protein, placing the nucleic acid in an expression cassette under the control of a particular promoter, and expressing the protein in a host cell. Recombinantly engineered cells known to those of skill in the art include, but are not limited of bacteria, yeast, plant, filamentous fungi, insect (especially employing baculoviral vectors) of mammalian cells.

The recombinant nucleic acids are operably linked to appropriate control sequences for expression in the selected host. For *E. coli*, example control sequences include the T7, trp, or lambda promoters, a ribosome binding site and, preferably, a transcription termination signal. For eukaryotic cells, the control sequences typically include a promoter and, preferably, an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods. Such methods include, for example, the calcium chloride transformation method for *E. coli* and the calcium phosphate treatment or electroporation methods for mammalian cells. Cells transformed by the plasmids can be selected by resistance to antibiotics conferred by genes contained on the plasmids, such as the amp, gpt, neo, and hyg genes.

Once expressed, the recombinant peptides can be purified according to standard procedures of the art, including ammonium sulfate precipitation, affinity columns, column chromatography, gel electrophoresis and the like (see, e.g., Scopes, *Polypeptide Purification* (1982); Deutscher, *Methods in Enzymology* Vol. 182: *Guide to Polypeptide Purification* (1990)). Once purified, partially or to homogeneity as desired, the NAP and ADNF polypeptides may then be used, e.g., to prevent neuronal cell death or as immunogens for antibody production. Optional additional steps include isolating the expressed protein to a higher degree, and, if required, cleaving or otherwise modifying the peptide, including optionally generating the protein.

After chemical synthesis, biological expression or purification, the peptide(s) may possess a conformation substantially different than the native conformations of the constituent peptides. In is case, it is helpful to denature and reduce the peptide and then to cause the peptide to re-fold into the preferred conformation, Methods of reducing and denaturing peptides and inducing re-folding are well known to those of skill in the art (see Debinski et al., *Biol. Chem.* 268:14065-14070 (1993); Kreitman & Pastan, *Bioconjug. Chem.* 4:585 (1993); and Buchner et al., *Anal Biochem.* 205:263-270 (1992)). Debinski et al., for example, describe the denaturation and reduction of inclusion body peptides in guanidine-DTE. The peptide is then refolded in a redox buffer containing oxidized glutathione and L-arginine.

One of skill will recognize that modifications can be made to the peptides without diminishing their biological activity. Some modifications may be made to facilitate the cloning, expression, or incorporation of the targeting molecule into a fusion peptide. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Use of NAP and ADNF Polypeptides for Treating Anxiety and/or Depression, Including Other Mood Disorders and Anxiety Disorders This invention discloses for the first time the surprising finding that NAP and ADNF polypeptides that were shown before to be neuroprotective and providing cognitive enhancements can be used in the treatment and/or prevention of a broad range of human clinical disorders such as anxiety and depression and a broad range of related disorders. As current medications used for treatment of anxiety disorders may adversely affect alertness, this surprising discovery offers an obvious advantage. Furthermore, anxiety is common in the elderly and can present as a primary anxiety disorder or as a symptom of another disorder. Generalized anxiety disorder (GAD), in particular, is a common syndrome in late life. Anxiety symptoms are also common features of late-life depression and dementia.

Treatment of anxiety in elderly persons has typically involved the use of benzodiazepines, which are often effective but problematic because they are associated with increased risk of cognitive impairment, falls, and fractures (Lenze et al., *CNS Spectr.* 12 Suppl 3:6-13 (2003)). Benzodiazepines interact with the gamma-aminobutyric acid (GABA) receptor. Previously, gephyrin, a tubulin-binding protein, was found as the core of inhibitory postsynaptic scaffolds stabilizing glycine receptors (GlyRs) and/or GABA (A) receptors (Hanus, et al., *J. Neurosci.* 24(5):1119-28 (2004)). Here, a mechanism for NAP is disclosed and the molecular target—tubulin, the subunit protein of microtubules is identified as the NAP binding protein. The direct interaction of NAP with tubulin may circumvent the adverse side effects associated with benzodiazepines treatments and further offers a target platform for novel drug discovery.

Anxiety is a cardinal symptom of many psychiatric disorders as well as a disease in itself. Symptoms of anxiety commonly are associated with depression and especially with dysthymic disorder (chronic depression of moderate severity), panic disorder, agoraphobia; and other specific phobias, obsessive-compulsive disorder, eating disorders and many personality disorders. Anxiety in human includes those further divisions set out in the *Diagnostic and Statistical Manual of Mental Disorders* (American Psychiatric Association, DSM-IV, 4th Ed. 1994).

Anxiety disorders are serious medical illnesses that affect approximately 19 million American adults. (Narrow et al., NIMH epidemiology note: prevalence of anxiety disorder. One-year prevalence best estimates calculated from ECA and NCS data. Population estimates based on U.S., Census estimated residential population age 18 to 54 on Jul. 1, 1998. Unpublished). These disorders fill people's lives with overwhelming anxiety and fear. Anxiety disorders are acute attacks or are chronic, relentless, and can grow progressively worse if not treated. Examples include: panic disorder, obsessive-compulsive disorder, attention deficit disorder and attention deficit hyperactivity disorder, post-traumatic stress disorder, social phobia (or social anxiety disorder), specific phobias, and generalized anxiety disorder.

Major depression is characterized by clinically significant depressions of mood and impairment of functioning as its primary clinical manifestations. Its clinical manifestations and current treatment overlap the anxiety disorders including panic-agorophobia syndrome, sever phobias, generalized anxiety disorder, social anxiety disorder, post-traumatic stress disorders and obsessive-compulsive disorder. Extremes of mood may be associated with psychosis, manifested as disordered or delusional thinking and perceptions, often congruent with the predominant mood.

In any given 1-year period, 9.5 percent of the population, or about 18.8 million American adults, suffer from a depressive illness (Robins & Regier (Eds). *Psychiatric Disorders in America, The Epidemiologic Catchment Area Study*, 1990; New York: The Free Press). Depression often accompanies anxiety disorders (Regier et al., *British Journal of Psychiatry Supplement* 34: 248 (199°)) and, when it does, it needs to be treated as well. Symptoms of depression include feelings of sadness, hopelessness, changes in appetite or seep, low energy, and difficulty concentrating. Most people with depression can be effectively treated with antidepressant medications, certain types of psychotherapy, or a combination of both.

Depressive disorders is expressed in different forms:

Major depression is manifested by a combination of symptoms (see symptom list) that interfere with the ability to work, study, sleep, eat, and enjoy once pleasurable activities. Such a disabling episode of depression may occur only once but more commonly occurs several times in a lifetime.

A less severe type of depression, dysthymia, involves long-term, chronic symptoms that do not disable, but keep one from functioning well or from feeling good. Many people with dysthymia also experience major depressive episodes at some time in their lives.

Another type of depression is bipolar disorder, also called manic-depressive illness. Not nearly as prevalent as other forms of depressive disorders, bipolar disorder is characterized by cycling mood changes: severe highs (mania) and lows (depression). Sometimes the mood switches are dramatic and rapid, but most open they are gradual. When in the depressed cycle, an individual can have any or all of the symptoms of a depressive disorder. When in the manic cycle, the individual may be overactive, overtalkative; and have a great deal of energy. Mania often affects thinking, judgment, and social behavior in ways that cause serious problems and embarrassment. For example, the individual in a manic phase may feel elated, full of grand schemes that might range from unwise business decisions to romantic sprees. Mania, left untreated, may worsen to a psychotic state.

Gamma-Aminobutyric acid (GABA) is the major inhibitory neurotransmitter in the mammalian Central Nervous System (CNS). GABA participates in the regulation of neuronal excitability through interaction with specific membrane proteins (the GABAA receptors). The binding of GABA to these postsynaptic receptors, results in an opening of a chloride channel integrated in the receptor which allows the entry of Cl— and consequently leads to hyperpolarization of the recipient cell. The action of GABA is allosterically modulated by a wide variety of chemical entities which interact with distinct binding sites at the GABAA receptor complex.

One of the most thoroughly investigated modulatory site is the benzodiazepine binding site. The benzodiazepines constitute a well-known class of therapeutics displaying hypnotic, anxiolytic and anticonvulsant effects. Their usefulness, however, is limited by a broad range of side effects comprising sedation ataxia, amnesia, alcohol and barbiturate potentiation, tolerance development and abuse potential. Consequently, there has been an intensive search for modulatory agents with an improved profile, and a diversity of chemical entities distinct from the benzodiazepines, but with GABA modulatory effects have been identified. The existence of endogenous ligands for the GABAA receptor complex beside GABA has often been described, but their role in the regulation of GABA action is still a matter of controversy.

The progress of molecular biology during the last decade has contributed enormously to the understanding of benzodiazepine receptor pharmacology. A total of 14 GABAA receptor subunits have been cloned from mammalian brain and have been expressed/co-expressed in stable cell lines. These transfected cells constitute an important tool in the characterization of subtype selective ligands. In spite of the rapidly expanding knowledge of the molecular and pharmacological mechanisms involved in GABA/benzodiazepine related CNS disorders, the identification of clinically selective acting drugs is still to come (Teuber et al., *Curr Pharm Des* 5(5): 317-43(1999)).

Control of neurotransmitter receptor expression and delivery to the postsynaptic membrane is of great importance for neural signal transduction at synapses. The GABA type A (GABA(A)) receptor-associated protein GABARAP was reported to have an important role for movement and sorting of GABA(A) receptor molecules to the postsynaptic membrane. GABARAP not only binds to GABA(A) receptor gamma2-subunit but also to tubulin, gephyrin, and ULK1, suggesting regulation through the interaction with the microtubular network (Stangler et al. *J Biol. Chem.* 19:277 (2002), 16:13363-6. Epub 2002 Mar. 1)

Anxiety is often defined as an organism's response to potential threat, as opposed to direct or immediate threat. Anxiety and depression also encompass disorders of mood such as affective disorders. The severity of these conditions covers an extraordinarily broad range from normal grief reactions and dysthymia to severe, incapacitating illnesses that may result in death.

Thus, according to the instant invention, NAP and ADNF polypeptides may be used to treat anxiety and/or depression and diseases or disorders related thereto, as defined herein.

Drug Discovery Using Nap-Tubulin Binding

The identification of tubulin as the NAP-biding site allows the use of tubulin and tubulin—derived peptides as targets for further drug discovery. e.g., for the treatment of diseases related to ADNF polypeptides such as anxiety, depression, disease related to neuronal cell death and oxidative stress, neurodegenerative diseases such as Alzheimer's disease, AIDS-related dementia, Huntington's disease, and Parkinson's disease, HIV-related dementia complex, stroke, head trauma, cerebral palsy, conditions associated with fetal alcohol syndrome. Such therapeutics can also be used in methods of enhancing learning and memory both pre- and post-natally. Experiments can be carried out with the intact tubulin structure and NAP as a displacing agent or by further identification of the precise tubulin-NAP interacting site (e.g., as described Katchalski-Katzir et al., *Biophys Chem.* 100(1-3):293-305 (2003); Chang et al., *J Comput Chem*, 24(16):1987-98 (2003)).

Preliminary screens can be conducted by screening for agents capable of binding polypeptide of the invention, as at least some of the agents so identified are likely modulators of polypeptide activity. The binding assays usually involve contacting a polypeptide of the invention with one or more test agents and allowing sufficient time for the protein and test agents to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet and Yamamura (1985) *Neurotransmitter, Hormone or Drug Receptor Binding Methods*, in *Neurotransmitter Receptor Binding* (Yamamura et al., eds.), pp. 61-89. The protein utilized in such assays can be naturally expressed, cloned or synthesized.

Agents that are initially identified by any of the foregoing screening methods can be further tested to validate the apparent activity. Preferably such studies are conducted with suitable animal models. The basic format of such methods involves administering a lead compound identified during an initial screen to an animal that serves as a model for humans and then determining if expression or activity of a polynucleotide or polypeptide of the invention is in fact upregulated. The animal models utilized in validation studies generally are mammals of any kind. Specific examples of suitable animals include, but are not limited to, primates, mice, and rats. In one embodiment, the Elevated plus maze and the Morris water maze tests are used, as described in Example 1.

The agents teased as modulators of the polypeptides of the invention can be any small chemical compound, or a biological entity, such as a protein, sugar, nucleic acid, RNA, or lipid. Typically, test compounds will be small chemical molecules and peptides. Essentially, any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter in robotic assays). It will be appreciated that there are many suppliers of chemical compounds, including Sigma (St Louis, Mo.), Aldrich (St. Louis, Mo.), Sigma-Aldrich (St. Louis, Mo.), Fluka Chemika-Biochemica Analytika (Buchs, Switzerland) and the like. Modulators also include agents designed to reduce the level of mRNA of the invention (e.g. antisense molecules, ribozymes, DNAzymes and the like) or the level of translation from an mRNA.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (articular chemical species or subclasses) that display desired characteristic activity. The compounds thus identified can serve as conventional "lead compounds" or can themselves be used as potential or actual therapeutics. Libraries available for screening for small active molecules include the Available Chemical Directory (ACD, 278,000 compounds), ACD screening library (>1,000,000 compounds), CRC Combined Chemical Dictionary (~350, 000 compounds) Anisex (115,000 compounds) Maybridge (62,000 compounds) Derwent and NCI libraries.

Pharmaceutical Administration

The pharmaceutical compositions of the present invention are suitable for use in a variety of drug delivery systems. Peptides that have the ability to cross the blood brain barrier can be administered, e.g., systemically, nasally, etc., using methods known to those of skill in the art. Larger peptides that do not have the ability to cross the blood brain barrier can be a administered to the mammalian brain via intracerebroventricular (ICV) injection or via a cannula using techniques well known to those of skill in the art (see, e.g., Motta & Martini, *Proc. Soc. Exp. Biol. Med.* 168:62-64 (1981); Peterson et al., *Biochem. Pharmacol.* 31:2807-2810 (1982); Rzepczynski et al., *Metab. Brain Dis.* 3:211-216 (1939); Leibowitz et al., *Brain Res. Bull.* 21:905-912 (1988); Sramka et al., *Stereotact. Funct. Neurosurg.* 58:79-83 (1992); Peng et al., *Brain Res.* 632:57-67 (1993); Chem et al., *Exp. Neurol.* 125:72-81 (1994); Nikkhah et al., *Neuroscience* 63:57-72 (1994); Anderson et al., *J Comp. Neurol.* 357:196-317 (1995); and Brecknell & Fawcett, *Exp. Neurol.* 138:338-344 (1996)).

Suitable formulations for use in the present invention are found in Remington's *Pharmaceutical Sciences* (17th ed. 1985)), which is incorporated herein by reference. In addition, for a brief review of methods for drug delivery, see Langer, *Science* 249:1527-1533 (1990), which is incorporated herein by reference. Suitable dose ranges are described in the examples provided herein, as well as in WO 9611948, herein incorporated by reference in its entirety.

As such, the present invention provides for therapeutic compositions or medicaments comprising one or more of the NAP or ADNF polypeptides described hereinabove in combination with a pharmaceutically acceptable excipient, wherein the amount of the NAP or ADNF polypeptide is sufficient to provide a therapeutic effect.

In a therapeutic application, the NAP and ADNF polypeptides of the present invention are embodied in pharmaceutical compositions intended for administration by any effective means, including parenteral, topical, oral, pulmonary (e.g. by inhalation) or local administration. Preferably, the pharmaceutical compositions are administered parenterally, e.g., intravenously, subcutaneously, intradermally, or intramuscularly, or intranasally.

Thus, the invention provides compositions for parenteral administration that comprise a solution of NAP or ADNF polypeptide, as described above, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

For solid compositions, conventional nontoxic solid carriers may be used that include, for, example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and more preferably at a concentration of 25%-75%.

For aerosol administration, the NAP or ADNF polypeptides are preferably supplied in finely divided from along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery. An example includes a solution in which each milliliter included 7.5 mg NaCl, 1.7 mg citric acid monohydrate, 3 mg disodium phosphate dihydrate and 0.2 mg benzalkonium chloride solution (50%) (Gozes et al., *J Mol Neurosci.* 19(1-2):167-70 (2002)).

In therapeutic applications, the NAP or ADNF polypeptides of the invention are administered to a patient in an amount sufficient to reduce or eliminate symptoms of anxiety ad/or depression. An amount adequate to accomplish this is defined as "therapeutically effective dose." Amounts effective for this use will depend on, for example, the particular NAP or ADNF polypeptide employed, the type of disease or disorder to be prevented, the manner of administration, the weight and general state of health of the patient, and the judgement of the prescribing physician.

For example, an amount of polypeptide falling within the range of a 100 ng to 10 mg dose given intranasally once a day (e.g., in the evening) would be a therapeutically effective amount. Alternatively, dosages may be outside of this range, or on a different schedule. For example, dosages may range from 0.0001 mg/kg to 10,000 mg/kg, and will preferably be about 0.001 mg/kg, 0.1 mg/kg, 1 mg/kg 5 mg/kg, 50 mg/kg or 500 mg/1 g per dose. Doses may be administered hourly, every 4, 6 or 12 hours, with meals, daily, every 2, 3, 4, 5, 6, for 7 days, weekly, every 2, 3, 4 weeks, monthly or every 2, 3 or 4 months, or any combination thereof. The duration of dosing may be single (acute) dosing, or over the course of days, weeks, months, or years, depending on the condition to be treated. Those skilled in the art can determine the suitable dosage, and may rely on preliminary data reported in Gozes et al., 2000, Gozes et al., 2002), Bassan et al. 1999, Zemlyak et al.; *Regul. Pept.* 96:39-43 (2000); Brenneman et al., *Biochem, Soc. Trans.* 28: 452-455 (2000); *Erratum Biochem Soc. Trans.* 28:983; Wilkemeyer et al. *Proc Natl. Acad., Sci. USA* 100: 3543-8548 (2003)).

EXAMPLE 1

Intranasal Administration of Nap Decreases Anxiety-Like Behavior in Aging Mice in the Elevated Plus Maze The present study was designed to evaluate the long-term behavioral outcome of chronic intranasal exposure to NAP.

Methods

ND-Swiss male mice (8 months old; Harlan Sprague Dawley, Inc., Indianapolis, Ind.) were kept under a 12:12 hour light/dark regimen, with food and water available at all times. The mice were kept in the animal care facility of the Tel Aviv University in compliance with institutional and state guidelines.

NAP was custom synthesized by Peninsula (Bachem, Torrance, Calif., USA) or Peptide Technologies (Bethesda, Md., USA), The peptide was dissolved in a solution DD, in which each milliliter included 7.5 mg NaCl, 1.7 mg citric acid monohydrate, 3 mg disodium phosphate dihydrate and 0.2 mg benzalkonium chloride solution (50%). The peptide was administered intranasally every day, 5 days a week, 0.5 µg in 10 µl for each mouse, half the portion in each nostril. The control group received 10 µl of the inert carrier per day. The mice were treated at least 1 h prior to the daily experiment (water maze).

The elevated plus maze was built in a 'plus' from with two open arms (68×7.5×1 cm) and two closed arms (68×7.5×17.5 cm) opposing each other. The center of the four arms included a middle square (7.5×7.5 cm). The maze was elevated, at a height of 51 cm above ground level. Each mouse was placed separately in the center of the maze, facing an open arm. Each trial lasted 5 min. Parameters measured included: (1) Number of closed arms entries, an accepted index of motor function; (2) total number of open arms entries; (3) (length of time spent in the open arms; (4) length of time spent in the closed arms. An entry was counted only after the mouse entered the arm with all four paws. The percentage of open arm entries out of total arms entries and the percentage of time spent in the open arms, accepted measures of anxiety levels, were further calculated.

Mice were also subjected to two daily tests in a Morris water maze (diameter 90 cm; depth, 20 cm), as described in WO 01/092333, incorporated herein by reference. Latency to reach the hidden platform over a 90 second test period was recorded. The experiment was performed for 4-5 consecutive days. To measure motor functions, mice were placed on a platform for 30 seconds and then in the water facing the wall. The platform was then removed from the maze and the time spent by the mice in the pool's quarter where the platform used to be was recorded (for 90 seconds). Measurements were performed with the HVS video tracking system (HVS Image Ltd., Hampton, UK). The water maze was chose as a test as current medication against anxiety often present a side effect of reduced cognitive functions.

Statistical tests used one-way analysis of variance with pairwise multiple comparison procedure (Student—Newman—Kuels method). When only two groups were compared, the Student t-test was used.

Results

When tested in the elevated plus maze, at 13 months age, after 5 months of chronic treatment with NAP, the percentage of time spent in the open aims was significantly higher in the NAP-treated mice (FIG. 1a). However, the mean percentage of open arm entries out of total arms entries, the number of closed arms entries and the total number of arms entries was similar in the control group and the NAP-treated group (FIGS. 1b-1d).

Figure 2:
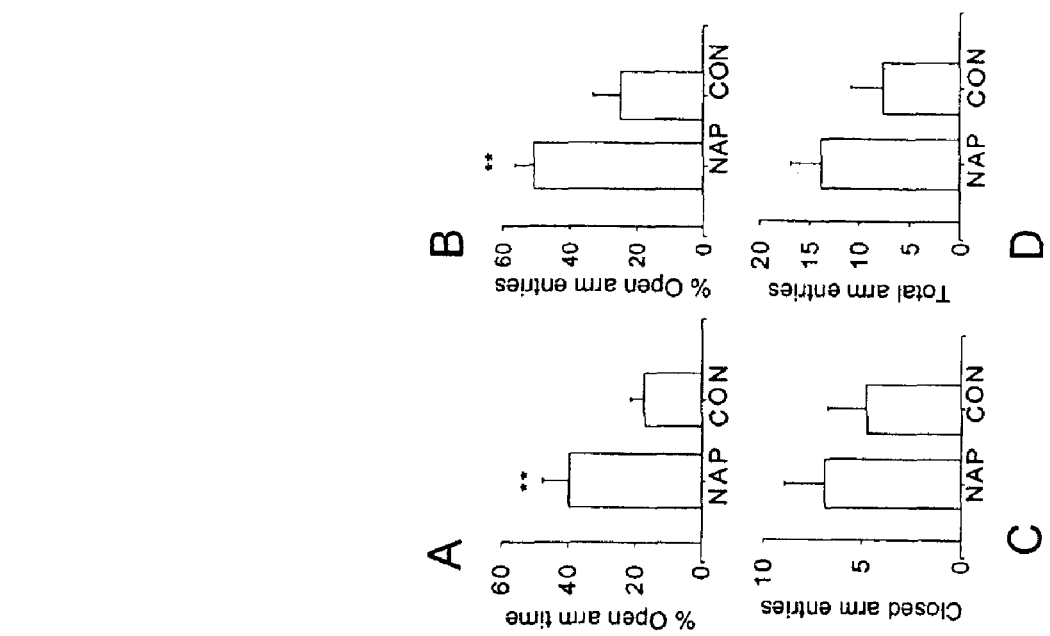
FIG. 2. Sixteen-month-old mice chronically treated (week days, daily for 8 months) with NAP are more relaxed than sham-treated mice. Experiments were performed as in FIG. 1A-D. NAP treated mice, n=11; control mice, n=10, (**p<0.01).

When the same group of mice was re-tested 3 months later at the age of 16 months and after 8 months of chronic intranasal treatments, again measurements indicated a decreased level of anxiety. The decreased anxiety level in the NAP-treated older mice was even more prominent than in the younger animals. Similar to the results in 13-month old mice, the percentage of time spent in the open arms by the 16-month old animals was significantly higher in the NAP-treated group as compared to the control group (FIG. 2a). However, in contrast to the younger mice that were treated with NAP for 5 months, in the older mice, treated for 8 months, the percentage of open arm entries out of total arms entries was significantly higher in the NAP treated mice (FIG. 2b). Motor function indices including the number of closed alms entries and the total amount of arms entries were not significantly different between the two groups (FIGS. 2c and 2d).

As anxiolytics tend to reduce leaning and memory fractions, long-term effects of NAP exposure were assessed in a spatial memory test using the Morris water maze paradigm. At the age of 15 months, and after 7 months of chronic intranasal NAP treatment an apparent improvement (measured over four testing days) was observed in the NAP-treated mice but not in the control mice, in the first daily trial, but not in the second daily trial (FIG. 3, A,B respectively). No significant differences were found when comparing the first to last daily trial in either group. Yet, a comparison of a block of the first daily trial in the first and the second testing days vs. a block of the first daily trials in the third and fourth testing days showed that only the NAP-treated mice were significantly faster in finding the platform in the last two days (second block) demonstrating learning ($p<0.04$). These experiments show a moderate improvement of spatial learning resulting from long-term exposure to intranasal NAP. No differences in motor behavior were apparent in eight month or 16-month-old mice measured as the time to reach the visible platform (24+7.6; NAP and 24+6.8; control, eight-month-old mice). Furthermore, only a small effect was seen at 15 months in the probe test, with the NAP-treated animals spending 25.8+3.4 sec/90 sec in the area of the pool where the platform used to be vs. 21.96+2.9 in the sham-treated mice.

In the elevated plus model, anxiety-like behavior is measured by the percentage of time spent in the open arms and the percentage of open arms entries. Curiosity will lead mice to spend more time in the open arms which anxiety will probably make them stay in the closed, protected arms of the model. The number of closed arms entries is an accepted parameter of motor function. Intranasal NAP significantly increased the percentage of time spent in the open arms and longer exposure to NAP also increased open arm entries, thus demonstrating reduced anxiety-like behavior in NAP treated mice. Furthermore, in spatial learning and memory tests, an effect was observed after long-term NAP administration in aged mice, on the first daily test, indicative of reference memory.

EXAMPLE 2

NAP Stabilizes Microtubules by Direct Association with Tubulin

The present study was conducted to identify primary targets for NAP for neuroprotection, and to identify NAP binding proteins.

Methods:

Cell cultures. Rat pheochromocytoma cells (PC12) were grown in Dulbecco's Modified Eagle's Medium (DMEM) supplemented with 8% fetal calf serum (FCS), 8% Horse donor serum, 2 mM glutamine, and 1% penicillin streptomycin solution for 48 h. NIH3T3 were grown in DMEM supplemented with 10% fetal calf serum (FCS), 2 mM L-Glutamine, 0.1 mg/ml streptomycin, 100 units/ml penicillin. For the experiments, cells were harvested resuspended and seeded in 96 well dishes at a concentration of 2×10(4) cells/well. The cells were allowed to attach to the dish for 3 h and were then exposed to 300 uM $H_2O_2$ for 24 h. When neuroprotective activity was tested, the peptides were added while seeding. Additional studies with nerve growth factor (NGF, 0.1 ug/ml)-treated PC12 cells plated on collagen (100 ug/ml) were conducted. In these experiments, nerve growth factor (NGF) was added at seeding.

Rat cerebral cortical cells from newborn pups were prepared as before (Bassan et al., 1999). All procedures performed in these studies were conducted in accordance with the Tel Aviv University regulations and were approved by the Animal Care and Use Committee of Tel Aviv University. The use of animals was not excessive and no animal suffering occurred. In short, cerebral cortical tissue was incubated for 20 minutes at 37° C. in Hanks' balanced salt solution+15 mM HEPES, pH 7.3 containing trypsin B (Biological Industries, Beit Haemek, Israel). Dissociated cerebral cortical cells were added to the culture dish with 5% horse serum in DMEM. Cells were plated in a ratio of 1 cortex per two 75 $cm^2$ cell culture flasks (polystyrene, Corning, N.Y.). The medium was changed 1 day after plating. For astrocyte cultures, cells were split after 10 incubation days and plated in 24 well plates (each flask into 60 wells containing microscope cover glasses (12 mm diameter) and 250 µl medium). Cells were then incubated two additional weeks. For mixed neuroglial cultures, dissociated cerebral cortical cells were plated on a bed of astrocytes 2 weeks after the split and incubated in neuron-specific medium as before (Bassan et al., 1999; Brenneman, & Gozes, *J. Clin. Invest.* 97:2299-2307 (1996); based on Forsythe & Westbrook, *J. Physiol.* 396:515-533 (1988)).

Metabolic activity measurements. Metabolic activity of viable cells in culture was measured by a calorimetric method using a tetrazolium compound [3-(4,5-dimethylthiazol-2-yl-5-(3-carboxymethoxyphenyl)-2-(4-sulfophenyl)-2H tetrazolium, MTS] and an electron-coupling reagent phenazine methasulfate (PMS). MTS is bio-reduced by the living cells to the Formazan form that is detected at 490 nm (Promega, Madison, Wis.).

Affi-Gel 10 NAP affinity chromatography. A protein lysate was prepared from one-day-old rat brains in a buffer containing the following ingredients: 150 mM NaCl, 1 mM EDTA, 50 mM Tris-HCl, ph 4.5, 0.1% Triton X-100, 1% NP40 and a protease inhibitor cocktail (Roche Diagnostics, Mannheim, Germany). DNA was fragmented by sonication. Cell debris was discarded following 30 minutes centrifugation at 30,000×g. An affinity column containing NAP was prepared using elongated NAP (KKKGGNAPVSIPQC (SEQ ID NO:21) and Affi-Gel 10 in 0.2M $NaHCO_3$/0.5 M NaCl, pH 7.5. Further column preparation was according to the manufacturer's instructions (Amersham Pharmacia Biotech, AB, Uppsala). The brain extract prepared as above was loaded (2 mg/ml) on the column at 20° C. and incubated for an hour; the column was then washed with PBS until all unbound protein eluted as confirmed by protein assay (Bradford, BioRad, Mannheim). NAP-binding proteins were eluted in 0.1 M glycine (pH 3.0); the eluted protein fractions were then adjusted to pH 7.5 with Tris-HCl buffer. Electrophoresis on a 12% polyacrylamide SDS-containing gel was performed as before (Zamostiano et al., 2001).

Sulfolink coupling gel NAP affinity chromatography. The Second isolation efforts utilized a different affinity column, sulfolink coupling gel (Pierce, Rockford, Ill.). Binding of CKKGGNAPVSIPQ (SEQ ID NO:22) was performed according to the manufacturer's instruction. Brain extract was prepared as above and binding was performed at 4° C. for 20 h, washing was as above and bound proteins were eluted by incubation in the presence of excess soluble NAP (NAPVSIPQ; SEQ ID NO:2) 2 mg/ml PBS (2 ml/2 ml column) at 4° C. for 20 hours.

Sequence analysis. To further identify NAP binding protein(s) the polyacrylamide gel portion containing the affinity purified protein bands was subjected to in-gel proteolysis with trypsin and mass spectrometry analysis (Technion, Israel Institute of Technology, Smoler Protein Center, Department of Biology).

Direct NAP binding to proteins assessed by dot blot analysis. Each protein (tubulin or muscle actin (Sigma, Rehovot, Israel), or non-muscle actin from human platelets (Cytoskeleton, Denver, Colo.) was applied on nitrocellulose membrane (Schleicher & Schuell, Dassel, Germany) at a concentration of 1-4 microgram/1 microliter/spot and dried (45 min 20° C.). The membrane was incubated in a blocking solution (10 mM Tris, 6 mM NaCl, 0.05% Tween-20 and 10% lowfat milk) for 16 h at 4° C. Detection was with biotin-labeled NAP (Gottlieb et al., *Eur. J. Biochem.* 125:631-638 (1982)) with excess amount of NAP (e.g., 5 microgram) added to tubulin (e.g., 1 microgram) or actin being attached to the membrane support). Avidin-horse radish peroxidase conjugate and ECL+ (Western blotting detection system, Amersham Pharmacia Biotech, Buckinghamshire, UK) was used for further identification of interacting molecules.

Confocal microscopy. Synthetic NAP or fluorescein-labeled NAP (FITC-NAP) was added to tissue culture cells (ascending concentrations) and incubated for 15 mins-24 hours. After incubation, cells were extensively washed and fixed in 4% paraformaldehyde. Following fixation, Triton X-100 (0.2% was added to allow antibody cellular penetration for mouse monoclonal tubulin antibodies (TUB 2.5; Gozes & Barnstable, *Proc. Natl. Acad. Sci. USA* 79:2579-2583 (1982)) and rhodamin-labeled secondary goat anti-mouse IgG (Jackson ImmunoResearch, West Grove, Pa.). For specific neuronal staining in primary neuronal cultures, mouse monoclonal tubulin antibodies TUB2.1 (Gozes & Barnstable, 1982) were used. Further neuronal identification was obtained by staining with antibodies against neuron specific enolase as before (Brenneman &. Gozes, 1996). Fluorescent cells were analyzed with a Zeiss confocal laser scanning microscope. Zeiss LSM 410 inverted (Oberkochen, Germany) is equipped with a 25-milliwatt krypton-argon laser (488 and 568 nm maximum lines). A 40×/1.2 W Apochromat water-immersion lens (Axiovert 135M, Zeiss) was utilized for all imaging.

Microtubule assembly. A microtubule assembly kit Cyto-DYNAMIX Screen 01(CDS01) was obtained from Cytoskeleton (Denver, Colo.). Bovine MAP-rich tubulin (HTS01) was resuspended in G-PEM buffer (80 mM PIPES pH 69, 1 mM $MgCl$, 1 mM EGTA and 1 mM GTP) and subjected to polymerization at 37° C. The reaction was performed in 96-well plate. Assembly was monitored with a spectrophotometer SPECTRAmax 190 (Molecular Devices, Sunnyvale, Calif.) employing continuous recording at 350 nm.

Results

In this example, affinity chromatography of brain extracts identified tubulin, the brain major protein and subunit protein of the microtubules as a NAP-binding ligand. Microtubules have been shown before to be associated with the mechanism of anxiety-associated neurotransmission ((Stangler et al., 2002). In addition, NAP binding to non-muscle actin was also detected, suggesting interaction with polymerizing proteins. Tubulin and non-muscle actin NAP binding was also confirmed by dot blot analysis. In a cell free system, NAP stimulated tubulin assembly into microtubules. When added to cerebral cortical astrocytes, mixed neuroglial cultures or pheochromocytoma cells (a neuronal-like model), NAP caused rapid microtubule re-organization into distinct microtubular structures. Furthermore, treatment of astrocytes with $ZnCl_2$ that induces the formation of tubulin Zinc sheets (Melki & Carlier, *Biochemistry* 32(13):3405-13 (1993)) induced cell death as suggested before (Juarranz et al., *Photochem Photobiol.* 73(3):283-9 (2001); Haase et al., *Biol. Chem.* 382(8): 1227-34 (2001); Lobner et al. *Cell Mol Biol* Noisy-le-grand) 46(4):797-806 (2000)). Co-treatment with NAP inhibited the Zn-associated death. These functional results support the role of NAP as a microtubule stabilizing agent by direct association with tubulin. As depression may be associated with cell death (Eilat et al., *J Immunol.* 163(1): 533-4 (1999)) the neuroprotective properties of NAP, through interaction with key cytoskeletal elements is suggested to protect against anxiety, NAP structure is a random coil and it may require a conformational epitope on a tubulin for it's catalytic-like activity enucleating tubulin polymerization. Regardless, the tubulin interaction site for NAP offers a target platform for drug discovery against anxiety-like conditions.

NAP specificity: In order to test for NAP specificity and establish the identity of cell symptoms relevant for NAP activity tests, a number of cell fines were screened. The rat pheochromocytoma (PC12) cell line (a neuronal-like cell system) responded to NAP neuroprotection against the effects of oxidative stress (see also Steingart et al. *J. Mol. Neurosci.* 15:137-145 (2000)). Cells that did not respond to NAP included African green monkey kidney cell (COS-7), adenocarcinoma cells from human breast (MCF-7) and human colon (HT-29), human fibroblasts (BJ) as well as mouse fibroblasts (NIH3T3). No cell proliferation effect was seen on any of the above tested cell lines (Gozes et al., *J Mol Neurosci.* 20(3):315-22 (2003)). These results imply specificity for NAP's activity and suggest a NAP binding protein of neuronal lineage origin.

Isolation of NAP binding proteins by affinity chromatography: Based on the previous, results, brain homogenates were chosen as a putative enriched source for NAP interacting molecules. Extracts were subjected to affinity chromatography comprising NAP bound either Affi-Gel 10 or sulfolink coupling gel, two different solid supports. Elution of the NAP interacting molecules was obtained by either reducing the pH or by competing the binding to the insoluble NAP with excess free soluble NAP. Electrophoresis on a 12% polyacrylamide SDS-containing gel revealed a purified protein band at about 50,000 Dalton and an additional protein at about 42,000 Dalton.

Tubulin and actin are NAP binding proteins: When the gel portions containing the purified protein bands were submitted to in gel proteolysis with trypsin followed by mass spectrometry analysis, the ~50,000 Dalton NAP-binding protein was identified as rat alpha tubulin (molecular mass 50,242); gi223556, the second band identified was beta actin, mass 41,737, gi450885. The identification of tubulin included the characterization of 6 different tryptic peptides.

A dot blot assay on a cellulose nitrate filter was performed with spotted muscle and non-muscle actin and tubulin (1 microgram protein/microliter/spot). Results indicated binding to brain tubulin and to non-muscle actin, while no interaction with muscle actin was detected.

NAP interaction with tubulin/microtubules: confocal microscopy. To further establish an association between tubulin and NAP in the living cell, confocal microscopy analysis of fluorescent NAP and immunodetection of tubulin was performed. As a first experiment, PC12 cells and NIH3T3 cells 2 h after exposure to NAP were analyzed. Tubulin is a heterodimer composed of two related but non-identical, ~55-kDa subunits, α- and β-tubulin that exhibit microheterogeneity (Gozes & Littauer, Nature 276(5686):411-3 (1978); Gozes & Sweadner, Nature 294(5840):477-80 (1981)). To visualize the microtubule structure, monoclonal beta tubulin antibodies (TUB2.5; Gozes & Barnstable, Proc. Natl. Acad. Sci. USA 79:2579-2583 (1982)) were used. Results have shown that in PC12 cells, the microtubules seemed to assume a more definitive structure after NAP application. In contrast, in cells not responsive to NAP, such as NIH3T3 cells, no apparent change in the microtubule organization was observed.

To study microtubule rearrangement in differentiated neuronal-like PC12, cells were exposed to nerve growth factor (NGF). Results indicated robust microtubule rearrangement (100% of the cells) in these differentiated PC12 cells as well.

Two additional cell populations were tested: astrocytes as well as mixed astrocytes and neurons from newborn rat cerebral cortex. Either fluoresceine-labeled NAP (FITC-NAP) or native NAP was added to two-week-old astrocyte cultures and to one-week-old neuronal cultures originally plated on a bed of astrocytes. Astrocytes were used as a model, since previous results have indicated that while nanomolar concentrations of NAP protected neuronal-enriched cultures against beta amyloid toxicity (Zemlyak et al., 2000); a more potent protection at femtomolar concentrations of NAP was observed when neurons were plated on a bed of astrocytes (Bassan et al., 1999). In astrocytes, like in the PC12 cells, an effect of microtubule re-organization was observed. A time course experiment suggested that the microtubule re-organization effect was occurring 2 h after NAP application, with the microtubules undergoing an additional condensation 4 h after NAP application and returning to the original morphology 24 h after NAP application. Mitotic spindles were not apparent. Similar microtubule re-organizations were observed with NAP at concentrations ranging from $10^{-15}$ M-$10^{-10}$ M with fluoresceine-labeled and with native NAP. Evaluation of the number of cells undergoing microtubule re-organization following NAP treatment showed maximal organization at 2-4 h with a decline at 24 h.

A control peptide, C2 (VLGGGSALL) (SEQ ID NO:23) that does not protect neurons in vitro did not induce a microtubule-associated morphological change.

Detection of fluoresceine labeled NAP inside cells: NAP can internalize cells and exhibit structural similarity to proteins/peptides used to permeate membranes: After a 2 h incubation period at 37° C., fluoresceine-labeled NAP was detected inside the cell. A critical question is whether NAP induces microtubule re-organization through interaction with a surface receptor, or is a pore-forming peptide that interacts with the lipid bilayer and is then internalized into cells. To evaluate potential surface labeling, initial incubation was carried out at 4° C. and in a parallel experiment at pH 3.0. When NAP ($10^{-15}$ M) was incubated with astrocytes at pH 3.0 for 15 minutes, microtubule reorganization was apparent and fluoresceine, labeled NAP was visualized inside the cells. At 4° C., while microtubule reorganization did not take place, as microtubules undergo disassembly at 4° C., a dose-dependent intracellular accumulation of NAP was apparent.

NAP structural analysis suggest similarities to peptides/proteins that transverse the cellular membrane, such as the VP22 translocation domain from HSV and signal peptides such as the Kaposi fibroblast growth factor (K-FGF) region. Bacterial toxins such as the C. perfringens iota toxin, diphtheria toxin, Pseudomonas exotoxin A, pertussis toxin, and B. anthracis toxin can deliver translocate peptide through the cell membrane.—Do we need references here?

Changes in neuronal morphology toward a differentiated neuronal structures (neurotorphism): Previous results indicated that NAP protects neurons (e.g., Bassan et al., 1999). In the assay system of mixed cerebral cortical cells from newborn rat brains, the effect of NAP on the microtubule system was tested. Results, using confocal microscopy as above, identified fluorescent NAP in the neurons. These studies were extended to determine the degree of microtubule re-organization in the neurons using the tubulin monoclonal antibody TBU2.1 that shows preferential binding to neuronal tubulin (Gozes & Barnstable, 1982) as verified by standing with antibodies directed against neuron-specific enolase. Here, results showed extensive microtubule re-organization in the NAP-treated neurons. Further quantitations indicated that of 145 neurons counted in the control (untreated neurons) only 4 neurons exhibited a similar microtubule arrangement to that seen 2 h after, $10^{-15}$ M NAP treatment. After NAP treatment, out of 213 cells counted, 208 exhibited the NAP-related re-rearrangement, suggesting an effect on ~97% of the treated neurons, Statistical analysis of the changes in neuronal morphology (number of processes per cell) indicated that in untreated neurons the number was 2.56+/−0.14/cell (mean+/−SEM, in 62 neurons). In NAP-treated neurons the number of processes was 6.47+/−0.3 (mean=+/−SEM, in 64 neurons, as also found in NAP 2 h-neurites). The difference was significant ($P<0.001$, student's t-test).

NAP promotes tubulin assembly; Using a high through-put analysis kit containing bovine tubulin (Cytoskeleton, Inc.), tubulin assembly was determined in the presence of increasing NAP concentrations, Measurements included absorbance determinations at 350 nm. While $10^{-18}$ M NAP did not influence microtubule assembly in the test tube, $10^{-15}$ M NAP stimulated microtubule assembly in a similar way to paclitaxel. Paclitaxel and taxol-like compounds have been suggested as possible neuroprotective agents, however, brain penetration issues and toxic side effects may exist (Rice et al., J Mol Neurosci. 20(3):339-43 (2003)). In contrast, NAP toxicology studies to-date indicate no adverse side effects (Gozes et al., 2000; Gozes et al., 2003). Further studies also indicate NAP brain penetration (Gozes et al., 2000) following intranasal, administration using either radiolabeled NAP (Gozes et al., 2000) or mass spectrometry validated assays. NAP at $10^{-10}$ M promoted tubulin assembly t the same degree as at a concentration of $10^{-15}$ M. At higher concentrations of $10^{-8}$ M NAP, no significant stimulation was observed over the 40 minutes assembly period at 37° C., paralleling the dose dependent survival-promoting response curve. Paclitaxel was used as a positive control and C2 a peptide that was utilized as a negative control in the cellular assay did not affect microtubule assembly as well.

Tubulin as a discover platform for neuroprotective and anxiolytic drug discovery: Results demonstrated that NAP cellular protection is specific and is paralleled by microtubule re-organization in glial cells and in differentiated neurons. A potential mechanism of action involves internalization into cells without a classical peptide receptor, followed direct binding to tubulin and acceleration of microtubule formation. Because NAP activity is selective for cells of neuronal origin (PC12) not fibroblasts (NIH3T3) as well as to astrocytes, it suggests tubulin/microtubule microheterogeneity in these cells that is specific for NAP's activity (Gozes et al., 1978 and 2981). Microheterogeneity may result from expression of different tubulin isotypes in different cells, or it may result from post-translational modifications, or both. The NAP doses required for tubulin polymerization concurred with the doses required for cellular protection against oxidative stress. NAP and related peptide protection against anxiety, depression, and other anxiety disorders and mood disorders may be direct through interaction with the microtubular network or indirect through glial and neuroprotection.

The examples set out above are intended to be exemplary of the effects of the invention, and are not intended to limit the embodiments or scope of the invention contemplated by the claims set out below. Other variants of the invention will be readily apparent to one of ordinary skill in the art and are encompassed by the appended claims. All publications, databases, Genbank sequences, GO terms, patents, and patent applications cited herein are hereby incorporated by reference.

This application is related to PCT WO 1/92333; U.S. Ser. No. 07/871,973 filed Apr. 22, 1992, now U.S. Pat. No. 5,767, 240; U.S. Ser. No. 08/342,297, filed Oct. 17, 1994 (published as WO96/11948), now U.S. Pat. No. 6,174,862; U.S. Ser. No. 60/037,404, filed Feb. 7, 1997 (published as WO98/35042); U.S. Ser. No. 09/187,330, filed Nov. 11, 1998(published as WO00/27875); U.S. Ser. No. 09/267,511, filed Mar. 12, 1999 (published as WO01/532117); U.S. Pat. No. 6,613,740, U.S. Ser. No. 60/149,956, filed Aug. 18, 1999 (published as WO01/2654); U.S. Ser. No. 60/208,944, filed May 31, 2000; and U.S. Ser. No. 60/267,805, filed Feb. 8, 2001; herein each incorporated by reference in their entirety.

What is claimed is:

1. A method of treating schizophrenia in a subject in need thereof, the method comprising the step of administering a therapeutically effective amount of an ADNF III polypeptide comprising an active core site having the following amino acid sequence:
Asn-Ala-Pro-Val-Ser-Ile-Pro-Gln (SEQ ID NO:2) to the subject.

2. The method of claim 1, wherein the ADNF III polypeptide is a full length human ADNF III polypeptide.

3. The method of claim 1, wherein the ADNF III polypeptide has the formula $(R^1)_x$-Asn-Ala-Pro-Val-Ser-Ile-Pro-Gln-$(R^2)_y$ (SEQ ID NO:13) in which
   $R^1$ is an amino acid sequence comprising from 1 to about 40 amino acids wherein each amino acid is independently selected from the group consisting of naturally occurring amino acids and amino acid analogs;
   $R^2$ is an amino acid sequence comprising from 1 to about 40 amino acids wherein each amino acid is independently selected from the group consisting of naturally occurring amino acids and amino acid analogs; and
   x and y are independently selected and are equal to zero or one.

4. The method of claim 1, wherein the ADNF III polypeptide is Asn-Ala-Pro-Val-Ser-Ile-Pro-Gln (SEQ ID NO:2).

5. The method of claim 1, wherein the active core site of the ADNF III polypeptide comprises at least one D-amino acid.

6. The method of claim 1, wherein the active core site of the ADNF III polypeptide comprises all D-amino acids.

7. The method of claim 1, wherein the ADNF III polypeptide is a member selected from the group consisting of:

(SEQ ID NO:9)
Gly-Gly-Asn-Ala-Pro-Val-Ser-Ile-Pro-Gln;

(SEQ ID NO:10)
Leu-Gly-Gly-Asn-Ala-Pro-Val-Ser-Ile-Pro-Gln-Gln-Ser;

(SEQ ID NO:11)
Leu-Gly-Leu-Gly-Gly-Asn-Ala-Pro-Val-Ser-Ile-Pro-Gln-Gln-Ser;

(SEQ ID NO:12)
Ser-Val-Arg-Leu-Gly-Leu-Gly-Gly-Asn-Ala-Pro-Val-Ser-Ile-Pro-Gln-Gln-Ser;
and (SEQ ID NO:2)
Asn-Ala-Pro-Val-Ser-Ile-Pro-Gln.

8. The method of claim 1, wherein the ADNF III polypeptide comprises up to about 20 amino acids at least one of the N-terminus and the C-terminus of the active core site.

9. The method of claim 1, wherein the ADNF III polypeptide contains a covalently bound lipophilic moiety to enhance penetration or activity.

10. The method of claim 1, wherein the ADNF III polypeptide is administered intranasally.

11. The method of claim 1, wherein the ADNF III polypeptide is administered orally.

12. The method of claim 1, wherein the ADNF III polypeptide is administered intravenously or subcutaneously.

* * * * *